US011208461B2

(12) United States Patent
Chiron-Blondel et al.

(10) Patent No.: US 11,208,461 B2
(45) Date of Patent: Dec. 28, 2021

(54) METHOD FOR PREDICTING THE OUTCOME OF A TREATMENT WITH AFLIBERCEPT OF A PATIENT SUSPECTED TO SUFFER FROM A CANCER

(71) Applicant: SANOFI, Paris (FR)

(72) Inventors: Marielle Chiron-Blondel, Paris (FR); Diether Lambrechts, Leuven (BE); Emmanuelle Magherini, Ris Orangis (FR); Vincent Thuillier, Bures sur Yvette (FR)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 16/663,000

(22) Filed: Oct. 24, 2019

(65) Prior Publication Data
US 2020/0157181 A1 May 21, 2020

Related U.S. Application Data

(60) Division of application No. 15/408,827, filed on Jan. 18, 2017, now Pat. No. 10,501,523, which is a continuation of application No. PCT/EP2015/066262, filed on Jul. 16, 2015.

(30) Foreign Application Priority Data

Jul. 18, 2014 (EP) .................................... 14306172

(51) Int. Cl.
C07K 14/71 (2006.01)
G01N 33/574 (2006.01)
A61K 9/00 (2006.01)
A61K 38/00 (2006.01)
A61K 31/282 (2006.01)
A61K 31/4745 (2006.01)
A61K 31/513 (2006.01)
A61K 31/519 (2006.01)

(52) U.S. Cl.
CPC ............ C07K 14/71 (2013.01); A61K 9/0019 (2013.01); A61K 31/282 (2013.01); A61K 31/4745 (2013.01); A61K 31/513 (2013.01); A61K 31/519 (2013.01); G01N 33/57419 (2013.01); A61K 38/00 (2013.01); C07K 2319/30 (2013.01); G01N 2333/5421 (2013.01); G01N 2800/52 (2013.01)

(58) Field of Classification Search
None
See application file for complete search history.

(56) References Cited

U.S. PATENT DOCUMENTS

| 4,353,887 A | 10/1982 | Hess et al. |
| 4,604,463 A | 8/1986 | Miyasaka et al. |
| 5,399,670 A | 3/1995 | Bhattacharya et al. |
| 5,474,796 A | 12/1995 | Brennan |
| 5,712,380 A | 1/1998 | Kendall et al. |
| 5,763,401 A | 6/1998 | Nayar |
| 5,851,999 A | 12/1998 | Ullrich et al. |
| 6,011,003 A | 1/2000 | Charnock-Jones et al. |
| 6,040,157 A | 3/2000 | Hu et al. |
| 6,100,071 A | 8/2000 | Davis-Smyth et al. |
| 6,121,230 A | 9/2000 | Charnock-Jones et al. |
| 6,267,958 B1 | 7/2001 | Andya et al. |
| 6,270,993 B1 | 8/2001 | Shibuya et al. |
| 6,342,219 B1 | 1/2002 | Thorpe et al. |
| 6,472,179 B2 | 10/2002 | Stahl et al. |
| 6,500,633 B1 | 12/2002 | Compton et al. |
| 6,524,583 B1 | 2/2003 | Thorpe et al. |
| 6,733,782 B1 | 5/2004 | Huet De Barochez et al. |
| 6,749,853 B1 | 6/2004 | Thorpe et al. |
| 6,811,779 B2 | 11/2004 | Rockwell et al. |
| 6,833,349 B2 | 12/2004 | Xia et al. |
| 6,875,432 B2 | 4/2005 | Liu et al. |
| 6,897,294 B2 | 5/2005 | Davis-Smyth et al. |
| 6,987,294 B2 | 1/2006 | Sasada et al. |
| 7,001,892 B1 | 2/2006 | Chmielewski et al. |
| 7,052,691 B2 | 5/2006 | Sleeman et al. |
| 7,060,268 B2 | 6/2006 | Andya et al. |
| 7,070,959 B1 | 7/2006 | Papadopoulos et al. |
| 7,087,411 B2 | 8/2006 | Daly et al. |
| 7,279,159 B2 | 10/2007 | Daly et al. |
| 7,300,653 B2 | 11/2007 | Wiegand et al. |
| 7,300,654 B2 | 11/2007 | Wiegand et al. |
| 7,303,746 B2 | 12/2007 | Wiegand et al. |
| 7,303,747 B2 | 12/2007 | Wiegand et al. |
| 7,303,748 B2 | 12/2007 | Wiegand et al. |

(Continued)

FOREIGN PATENT DOCUMENTS

| CN | 1968709 A | 5/2007 |
| DE | 197 24 793 A1 | 12/1998 |
| DE | 198 41 985 A1 | 3/2000 |
| EC | SP014068 | 2/2002 |
| EC | SP099404 | 7/2009 |
| FR | 2462908 A1 | 2/1981 |
| JP | S60-19790 A | 1/1985 |
| JP | H1180024 A | 3/1999 |
| JP | 2003-501089 A | 1/2003 |
| JP | 2007-500131 A | 1/2007 |
| JP | 2008-521866 A | 6/2008 |
| JP | 2010-532335 A | 10/2010 |
| JP | 6019790 B2 | 11/2016 |
| WO | WO 1993/000807 A1 | 1/1993 |
| WO | WO 1994/021679 A1 | 9/1994 |
| WO | WO 1996/031513 A1 | 10/1996 |

(Continued)

OTHER PUBLICATIONS

Shah et al. IL-8 as an underutilized prognostic factor in metastatic colorectal cancer. J. of Clin. Onc., 32, No. 3, Supp. 1. Abstract 409. 2014 (Year: 2014).*

(Continued)

Primary Examiner — Elly-Gerald Stoica
(74) Attorney, Agent, or Firm — Lathrop GPM LLP; James H. Velema; Judith L. Stone-Hulslander

(57) ABSTRACT

The present invention concerns the use of interleukin-8 (IL-8) as a biomarker for predicting the outcome of the treatment with aflibercept, or ziv-aflibercept of a patient suspected to suffer from a cancer.

10 Claims, 2 Drawing Sheets

Specification includes a Sequence Listing.

(56) References Cited

U.S. PATENT DOCUMENTS

| | | |
|---|---|---|
| 7,306,799 B2 | 12/2007 | Wiegand et al. |
| 7,351,411 B2 | 4/2008 | Holash et al. |
| 7,354,578 B2 | 4/2008 | Kandel et al. |
| 7,354,579 B2 | 4/2008 | Holash et al. |
| 7,354,580 B2 | 4/2008 | Cedarbaum |
| 7,354,581 B2 | 4/2008 | Cedarbaum et al. |
| 7,354,582 B2 | 4/2008 | Yung et al. |
| 7,374,757 B2 | 5/2008 | Papadopoulos et al. |
| 7,374,758 B2 | 5/2008 | Papadopoulos et al. |
| 7,378,095 B2 | 5/2008 | Cao et al. |
| 7,396,664 B2 | 7/2008 | Daly et al. |
| 7,399,612 B2 | 7/2008 | Daly et al. |
| 7,449,182 B2 | 11/2008 | Cedarbaum et al. |
| 7,479,272 B2 | 1/2009 | Cedarbaum |
| 7,479,273 B2 | 1/2009 | Cedarbaum |
| 7,479,274 B2 | 1/2009 | Cedarbaum |
| 7,479,275 B2 | 1/2009 | Cedarbaum |
| 7,482,001 B2 | 1/2009 | Cedarbaum |
| 7,482,002 B2 | 1/2009 | Cedarbaum |
| 7,521,049 B2 | 4/2009 | Wiegand et al. |
| 7,524,499 B2 | 4/2009 | Papadopoulos et al. |
| 7,531,172 B2 | 5/2009 | Stahl et al. |
| 7,531,173 B2 | 5/2009 | Wiegand et al. |
| 7,608,261 B2 | 10/2009 | Furfine et al. |
| 7,635,474 B2 | 12/2009 | Daly et al. |
| 7,704,500 B2 | 4/2010 | Papadopoulos et al. |
| 7,807,164 B2 | 10/2010 | Furfine et al. |
| 7,919,593 B2 | 4/2011 | Papadopoulos et al. |
| 7,964,377 B2 | 6/2011 | Papadopoulos et al. |
| 7,972,598 B2 | 7/2011 | Daly et al. |
| 8,029,791 B2 | 10/2011 | Papadopoulos et al. |
| 8,084,234 B2 | 12/2011 | Papadopoulos et al. |
| 8,092,803 B2 | 1/2012 | Furfine et al. |
| 8,110,546 B2 | 2/2012 | Dix et al. |
| 8,343,737 B2 | 1/2013 | Papadopoulos et al. |
| 8,388,963 B2 | 3/2013 | Vrignaud et al. |
| 8,404,638 B2 | 3/2013 | Dix et al. |
| 8,481,046 B2 | 7/2013 | Furfine et al. |
| 8,647,842 B2 | 2/2014 | Papadopoulos et al. |
| 8,710,004 B2 | 4/2014 | Dix et al. |
| 8,802,107 B2 | 8/2014 | Furfine et al. |
| 8,921,316 B2 | 12/2014 | Dix et al. |
| 9,139,644 B2 | 9/2015 | Papadopoulos et al. |
| 9,340,594 B2 | 5/2016 | Furfine et al. |
| 9,416,167 B2 | 8/2016 | Dix et al. |
| 9,511,140 B2 | 12/2016 | Dix et al. |
| 10,501,523 B2 | 12/2019 | Chiron-Blondel et al. |
| 2002/0004478 A1 | 1/2002 | Danko et al. |
| 2003/0017977 A1 | 1/2003 | Xia et al. |
| 2003/0092019 A1 | 5/2003 | Meyer et al. |
| 2003/0092606 A1 | 5/2003 | L'Italien et al. |
| 2003/0113316 A1 | 6/2003 | Kaisheva et al. |
| 2003/0144298 A1 | 7/2003 | Curwen et al. |
| 2003/0202972 A1 | 10/2003 | Andya et al. |
| 2004/0014667 A1 | 1/2004 | Daly et al. |
| 2004/0023864 A1 | 2/2004 | Roczniak et al. |
| 2004/0197324 A1 | 10/2004 | Liu et al. |
| 2004/0265309 A1 | 12/2004 | Kandel et al. |
| 2004/0266686 A1 | 12/2004 | Xia et al. |
| 2005/0032699 A1 | 2/2005 | Holash et al. |
| 2005/0043236 A1 | 2/2005 | Daly et al. |
| 2005/0112061 A1 | 5/2005 | Holash et al. |
| 2005/0175610 A1 | 8/2005 | Wiegand et al. |
| 2005/0196340 A1 | 9/2005 | Holash et al. |
| 2005/0196396 A1 | 9/2005 | Chen et al. |
| 2005/0260203 A1 | 11/2005 | Wiegand et al. |
| 2005/0276808 A1 | 12/2005 | Cedarbaum |
| 2005/0281822 A1 | 12/2005 | Cedarbaum et al. |
| 2005/0281831 A1 | 12/2005 | Davis-Smyth et al. |
| 2006/0030529 A1 | 2/2006 | Wiegand et al. |
| 2006/0058234 A1 | 3/2006 | Daly et al. |
| 2006/0148705 A1 | 7/2006 | Daly et al. |
| 2006/0172944 A1 | 8/2006 | Wiegand et al. |
| 2006/0178305 A1 | 8/2006 | Vrignaud et al. |
| 2006/0210566 A1 | 9/2006 | Holash et al. |
| 2006/0217311 A1 | 9/2006 | Dix et al. |
| 2007/0037748 A1 | 2/2007 | Stahl et al. |
| 2009/0062200 A1 | 3/2009 | Daly et al. |
| 2009/0081217 A1 | 3/2009 | Papadopoulos et al. |
| 2009/0105156 A1 | 4/2009 | Phiasivongsa et al. |
| 2009/0155899 A1 | 6/2009 | Papadopoulos et al. |
| 2009/0170925 A1* | 7/2009 | Nomoto ............ G01N 33/5011 514/450 |
| 2009/0234103 A1 | 9/2009 | Davis-Smyth et al. |
| 2010/0087632 A1 | 4/2010 | Daly et al. |
| 2010/0093552 A1 | 4/2010 | Panja |
| 2010/0160233 A1 | 6/2010 | Bissery et al. |
| 2010/0216168 A1 | 8/2010 | Heinzman et al. |
| 2010/0221782 A1 | 9/2010 | Papadopoulos et al. |
| 2011/0028698 A1 | 2/2011 | Papadopoulos et al. |
| 2011/0150903 A1 | 6/2011 | Baurin et al. |
| 2011/0176993 A1 | 7/2011 | Schneider |
| 2012/0264803 A1* | 10/2012 | Oka ..................... A61K 31/404 514/414 |
| 2013/0084635 A1 | 4/2013 | Papadopoulos et al. |
| 2013/0184205 A1 | 7/2013 | Vrignaud et al. |
| 2013/0330341 A1 | 12/2013 | Chiron Blondel et al. |
| 2013/0345322 A1* | 12/2013 | Cosgrave ......... G01N 33/57488 514/789 |
| 2014/0051642 A1 | 2/2014 | Castan |
| 2014/0127202 A1 | 5/2014 | Bissery et al. |
| 2015/0216795 A1 | 8/2015 | Assadourian et al. |
| 2016/0130320 A1 | 5/2016 | Papadopoulos et al. |
| 2016/0213608 A1 | 7/2016 | Furfine et al. |
| 2016/0244504 A1 | 8/2016 | Dix et al. |
| 2016/0244505 A1 | 8/2016 | Furfine et al. |
| 2017/0121387 A1 | 5/2017 | Chiron-Blondel et al. |
| 2018/0078496 A1 | 3/2018 | Assadourian et al. |
| 2018/0113134 A1 | 4/2018 | Dreymann et al. |
| 2019/0275147 A1 | 9/2019 | Bissery et al. |

FOREIGN PATENT DOCUMENTS

| | | |
|---|---|---|
| WO | WO 1997/044453 A1 | 11/1997 |
| WO | WO 1998/013071 A1 | 4/1998 |
| WO | WO 1999/003996 A1 | 1/1999 |
| WO | WO 1999/013909 A1 | 3/1999 |
| WO | WO 2000/034337 A1 | 6/2000 |
| WO | WO 2000/066125 A1 | 11/2000 |
| WO | WO 2000/075319 A1 | 12/2000 |
| WO | WO 2001/012416 A1 | 2/2001 |
| WO | WO 2001/085789 A2 | 11/2001 |
| WO | WO 2002/060489 A1 | 8/2002 |
| WO | WO 2003/074527 A1 | 9/2003 |
| WO | WO 2004/106378 A2 | 12/2004 |
| WO | WO 2004/110490 A2 | 12/2004 |
| WO | WO 2005/000220 A2 | 1/2005 |
| WO | WO 2005/000895 A2 | 1/2005 |
| WO | WO 2005/011734 A2 | 2/2005 |
| WO | WO 2005/020972 A2 | 3/2005 |
| WO | WO 2005/044540 A1 | 5/2005 |
| WO | WO 2005/072772 A1 | 8/2005 |
| WO | WO 2006/009809 A2 | 1/2006 |
| WO | WO 2006/047325 A1 | 5/2006 |
| WO | WO 2006/059012 A1 | 6/2006 |
| WO | WO 2006/104852 A2 | 10/2006 |
| WO | WO 2007/149334 A2 | 12/2007 |
| WO | WO 2008/076379 A2 | 6/2008 |
| WO | WO 2009/024667 A2 | 2/2009 |
| WO | WO 2009/073540 A2 | 6/2009 |
| WO | WO 2010/003853 A1 | 1/2010 |
| WO | WO 2010/022201 A2 | 2/2010 |
| WO | WO 2010/054110 A2 | 5/2010 |
| WO | WO 2010/112413 A1 | 10/2010 |
| WO | WO 2010/124264 A2 | 10/2010 |
| WO | WO 2011/014759 A2 | 2/2011 |
| WO | WO 2011/041441 A1 | 4/2011 |
| WO | WO 2012/146610 A1 | 11/2012 |

(56) References Cited

FOREIGN PATENT DOCUMENTS

| WO | WO 2016/008975 A1 | 1/2016 |
|---|---|---|
| WO | WO 2017/129537 A1 | 8/2017 |

OTHER PUBLICATIONS

Sanmamed et al. (Journal of Clinical Oncology, (May 20, 2014) vol. 32, No. 15, Supp. SUPPL. 1. Abstract No. e22135. (Year: 2014).*
Chakrabandhu B., The gastric mucosal tissue interleukin-8 mRNA expression level is a promising prognostic marker for prognosis prediction in advanced gastric cancer treatment. Cancer Research, (Apr. 15, 2013) vol. 73, No. 8, Supp. SUPPL 1. Abstract No. 3544. (Year: 2013).*
(2013) "Aflibercept", The Merck Index,15th Edition.
(2013) "Irinotecan", The Merck Index, 15th Edition.
(Dec. 10, 2010) "Declaration of Dr. Olin Gavin Thurston corresponding to the prosecution of European Patent Application No. EP04779050.6", 11 Pages.
(Jul. 3, 2012) "Center for Drug Evaluation and Research Medical Review", Medical Review(s), Application No. 125418orig1s000, 190 Pages.
Abajo, A, et al. (Jul. 10, 2012) "Identification of Predictive Circulating Biomarkers of Bevacizumab-Containing Regimen Efficacy in Pre-Treated Metastatic Colorectal Cancer Patients", British Journal of Cancer, vol. 107, No. 2, pp. 287-290.
Abajo, A, et al. (Nov. 9, 2010) "Dose-finding Study and Pharmacogenomic Analysis of Fixed-Rate Infusion of Gemcitabine, Irinotecan and Bevacizumab in Pretreated Metastatic Colorectal Cancer Patients", Br J Cancer. vol. 103, No. 10, pp. 1529-1535.
Allegra, Carmen Joseph., et al. (Jan. 31, 2017) "Effects of Prior Bevacizumab (B) use on Outcomes from the VELOUR Study: A Phase III study of Aflibercept (Afl) and FOLFIRI in Patients (pts) with Metastatic Colorectal Cancer (mCRC) after Failure of an Oxaliplatin Regimen", Journal of Clinical Oncology, vol. 30, No. 15_supplement Abstract 3505.
Allegra, Carmen Joseph., et al. (Sep. 22, 2016) "Meta-analysis of anti-VEGF class adverse events from three double-blind (Db) placebo (Pbo)-controlled phase III trials with IV aflibercept (Afl)", Journal of Clinical Oncology, vol. 30, No. 4_supplement, Abstract 561.
Altman, EM, et al. (Mar. 1999) "Diagnosis: Psoriasis or not? What are the Clues?", Seminars in Cutaneous Medicine and Surgery, vol. 18, No. 1, pp. 25-35.
André, T, et al. (Sep. 1999) "CPT-11 (Irinotecan) Addition to Bimonthly, High-Dose Leucovorin and Bolus and Continuous-Infusion 5-Fluorouracil (FOLFIRI) for Pretreated Metastatic Colorectal Cancer", European Journal of Cancer, vol. 35, Issue 9, pp. 1343-1347.
Antonelli, Alessandro (Jan. 12, 2002) "Anti-CD38 Autoimmunity in Patients with Chronic Autoimmune Thyroiditis or Graves' Disease", Clinical and Experimental Immunology, vol. 126, Issue 3, pp. 426-431.
Antonelli, Alessandro, et al. (Jul. 2004) "CD38 autoimmunity: Recent Advances and Relevance to Human Diabetes", Journal of Endocrinological Investigation, vol. 27, Issue 7, pp. 695-707.
Antonelli, Alessandro, et al. (May 2001) "Human Anti-CD38 Autoantibodies Raise Intracellular Calcium and Stimulate Insulin Release in Human Pancreatic Islets", Diabetes, vol. 50, No. 5, pp. 985-991.
Antonelli, Alessandro, et al. (Sep. 2002) "Autoimmunity to CD38 and GAD in Type I and Type II Diabetes: CD38 and HLA Genotypes and Clinical Phenotypes", Diabetologia, vol. 45, Issue 9, pp. 1298-1306.
Ashkenazi, et al. (1995) "Immunoadhesins: An Alternative to Human Monoclonal Antibodies", Methods, vol. 8, No. 2, pp. 104-115.
Autiero, Monica, et al. (2003) "Role of PIGF in the intra- and intermolecular cross talk between the VEGF receptors Flt1 and Flk1", Nature Medicine, vol. 9, pp. 936-943.

Baar, Joseph, et al. (May 15, 2009) "A Vasculature-Targeting Regimen of Preoperative Docetaxel with or without Bevacizumab for Locally Advanced Breast Cancer: Impact on Angiogenic Biomarkers", Clinical Cancer Research, vol. 15, Issue 10, pp. 3583-3590.
Barleon, Bernhard, et al. (Apr. 18, 1997) "Mapping of the Sites for Ligand Binding and Receptor Dimerization at the Extracellular Domain of the Vascular Endothelial Growth Factor Receptor FLT-1", The Journal of Biological Chemistry, vol. 272, No. 16, pp. 10382-10388.
Bartlett, David L. MD., et al. (Mar. 15, 2012) "Can Metastatic Colorectal Cancer Be Cured?", Home of the Journal Oncology, Cancer Network, vol. 26, No. 3, pp. 266-275.
Bender, Julia Glade., et al. (Sep. 15, 2012) "A Phase I Trial and Pharmacokinetic Study of Aflibercept (VEGF Trap) in Children with Refractory Solid Tumors: A Children's Oncology Group Phase I Consortium Report", Clinical Cancer Research, vol. 18, No. 18, pp. 5081-5089.
Blann, Andrew D., et al. (Feb. 1, 2002) "Vascular Endothelial Growth Factor and its Receptor, Flt-1, in the Plasma of Patients with Coronary or Peripheral Atherosclerosis, or Type II Diabetes", Clinical Science, vol. 102, No. 2, pp. 187-194.
Bork, P, et al. (Apr. 2000) "Powers and Pitfalls in Sequence Analysis: The 70% Hurdle", Genome Research, vol. 10, No. 4, pp. 398-400.
Bork, Peer, et al. (Oct. 1996) "Go Hunting in Sequence Databases but Watch out for the Traps", Trends in Genetics, vol. 12, Issue 10, pp. 425-427.
Brantley Jr, MA, et al. (Dec. 2007) "Association of Complement Factor H and LOC387715 Genotypes with Response of Exudative Age-Related Macular Degeneration to Intravitreal Bevacizumab", Ophthalmology, vol. 114, Issue 12, pp. 2168-2173.
Brattain, MG, et al. (May 1981) "Heterogeneity of Malignant Cells from a Human Colonic Carcinoma", Cancer Research, vol. 41, Issue 5, pp. 1751-1756.
Braun, AH, et al. (Mar. 18, 2004) "New Systemic Frontline Treatment for Metastatic Colorectal Carcinoma", Cancer, vol. 100, Issue 8, pp. 1558-1577.
Brawer, Michael K., et al. (Sep. 1998) "Measurement of complexed PSA improves specificity for early detection of prostate cancer", Urology, vol. 52, Issue 3, pp. 372-378.
Brenner, Steven E. (Apr. 1, 1999) "Errors in Genome Annotation", Trends in Genetics, vol. 15, Issue 4, pp. 132-133.
Brogan, Iain J., et al. (Dec. 1999) "Novel polymorphisms in the Promoter and 5' UTR Regions of the Human Vascular Endothelial Growth Factor Gene", Human Immunology, vol. 60, Issue 12, pp. 1245-1249.
Brown, L F., et al. (Nov. 1, 1992) "Expression of Vascular Permeability Factor (Vascular Endothelial Growth Factor) by Epidermal Keratinocytes During Wound Healing", Journal of Experimental Medicine, vol. 176, No. 5, pp. 1375-1379.
Brown, Lawrence F., et al. (May 1995) "Increased Expression of Vascular Permeability Factor (Vascular Endothelial Growth Factor) in Bullous Pemphigoid, Dermatitis Herpetiformis, and Erythema Multiforme", Journal of Investigative Dermatology, vol. 104, Issue 5, pp. 744-749.
Budman, Lorne I., et al. (Jun. 2008) "Biomarkers for Detection and Surveillance of Bladder Cancer", Canadian Urological Association Journal, vol. 2, No. 3, pp. 212-221.
Capizzi, RL (1996) "Curative Chemotherapy for Acute Myeloid Leukemia: The Development of High-Dose ara-C from the Laboratory to Bedside", Invest New Drugs, vol. 14, No. 3, pp. 249-256.
Carpenter, et al. (Aug. 1997) "Rational Design of Stable Lyophilized Protein Formulations: some Practical Advice", Pharmaceutical Research, vol. 14, No. 8, pp. 969-975.
Chiron, Marielle, et al. (Jun. 2014) "Differential Antitumor Activity of Aflibercept and Bevacizumab in Patient-Derived Xenograft Models of Colorectal Cancer", Molecular Cancer Therapeutics, vol. 13, Issue 6, pp. 1636-1644.
Chu, Quincy Siu-Chung., et al. (Jan. 16, 2009) "Aflibercept (AVE0005): An Alternative Strategy for Inhibiting Tumour Angiogenesis by Vascular Endothelial Growth Factors", Expert Opinion on Biological Therapy, vol. 9, Issue 2, pp. 263-271.

(56) References Cited

OTHER PUBLICATIONS

Chung, Michael, et al. (Jun. 2008) "Treatment of Malignant Ascites", Current Treatment Options in Oncology, vol. 9, pp. 215-233.
Commission Implementing Decision of 1.2.2013 granting marketing authorisation under Regulation (EC) No. 726/2004 of the European Parliament and of the Council for "ZALTRAP-aflibercept", European Commission, 45 Pages.
Cooper, M. E., et al. (Nov. 1999) "Increased Renal Expression of Vascular Endothelial Growth Factor (VEGF) and its Receptor VEGFR-2 in Experimental Diabetes", Diabetes, vol. 48, No. 11, pp. 2229-2239.
Corbett, et al. (1977) "Evaluation of Single Agents and Combinations of Chemotherapeutic Agents in Mouse Colon Carcinomas", Cancer, vol. 40, Serial 5, pp. 2660-2680.
Cunningham, Sonia A., et al. (Feb. 24, 1997) "Identification of the Extracellular Domains of Flt-1 That Mediate Ligand Interactions", Biochemical and Biophysical Research Communications, vol. 231, Issue 3, pp. 596-599.
Cutsem, Van E., et al. (Jun. 22, 2011) "Intravenous (IV) Aflibercept versus Placebo in Combination with Irinotecan/5-FU (FOLFIRI) for Second-Line Treatment of Metastatic Colorectal Cancer (MCRC): Results of a Multinational Phase III Trial (EFC10262 Velour)", Annals of Oncology, vol. 22, Supplement 5, Abstract O-0024, pp. V10-V18.
Cutsem, Van Eric., et al. (Apr. 18, 2011) "Cetuximab Plus Irinotecan, Fluorouracil, and Leucovorin as First-Line Treatment for Metastatic Colorectal Cancer: Updated Analysis of Overall Survival According to Tumour KRAS and BRAF Mutation Status", Journal of Clinical Oncology, vol. 29, No. 15, pp. 2011-2019.
Cutsem, Van Eric., et al. (Sep. 4, 2012) "Addition of Aflibercept to Fluorouracil, Leucovorin, and Irinotecan Improves Survival in a Phase III Randomized Trial in Patients with Metastatic Colorectal Cancer Previously Treated with an Oxaliplatin-Based Regimen", Journal of Clinical Oncology, vol. 30, No. 28, pp. 3499-3506.
Dassoulas, Konstantinos, et al. (Nov. 13, 2008) "Common polymorphisms in the vascular endothelial growth factor gene and colorectal cancer development, prognosis, and survival", Pharmacogenet Genomics, vol. 48, Issue 6, pp. 563-569.
Daugherty, et al. (Aug. 7, 2006) "Formulation and Delivery Issues for Monoclonal Antibody Therapeutics", Advanced Drug Delivery Reviews, vol. 58, No. 5-6, pp. 686-706.
Davis-Smyth, T, et al. (Feb. 6, 1998) "Mapping the Charged Residues in the Second Immunoglobulin-like Domain of the Vascular Endothelial Growth Factor/Placenta Growth Factor Receptor Flt-1 Required for Binding and Structural Stability", The Journal of Biological Chemistry, vol. 273, No. 6, pp. 3216-3222.
Davis-Smyth, T, et al. (Sep. 16, 1996) "The Second Immunoglobulin-Like Domain of the VEGF Tyrosine Kinase Receptor Flt-1 Determines Ligand Binding and may Initiate a Signal Transduction Cascade", The EMBO Journal, vol. 15, No. 18, pp. 4919-4927.
De Vries, et al. (Feb. 21, 1992) "The fms-like Tyrosine Kinase, a Receptor for Vascular Endothelial Growth Factor", Science, vol. 255, Issue 5047, pp. 989-991.
De Vriese, AN S., et al. (May 2001) "Antibodies against Vascular Endothelial Growth Factor Improve Early Renal Dysfunction in Experimental Diabetes", Journal of the American Society of Nephrology, vol. 12, No. 5, pp. 993-1000.
Declaration of Dr. Sarah Hymowitz submitted to the European Patent Office on Oct. 9, 2009, by Genentech, Inc. during prosecution of European Patent Appl. No. 05023819.5.
Delisser, Horace M., et al. (Oct. 1994) "Molecular and functional aspects of PECAM-1/CD31", Immunology Today, vol. 15, Issue 10, pp. 490-495.
Demolis, Pierre, et al. (2012) "Zaltrap Assessment report", European Medicines Agency, pp. 1-91.
Detmar, Michael, et al. (Jul. 1998) "Increased Microvascular Density and Enhanced Leukocyte Rolling and Adhesion in the Skin of VEGF Transgenic Mice", Journal of Investigative Dermatology, vol. 111, Issue 1, pp. 1-6.
Detmar, Michael, et al. (Sep. 1, 1994) "Overexpression of Vascular Permeability Factor/Vascular Endothelial Growth Factor and its Receptors in Psoriasis", Journal of Experimental Medicine, vol. 180, No. 3, pp. 1141-1146.
Doerks, T, et al. (Jun. 1, 1998) "Protein Annotation: Detective Work for Function Prediction", Trends in Genetics, vol. 14, Issue 6, pp. 248-250.
Duncan, R, et al. (Oct. 1994) "Polymer Conjugates. Pharmacokinetic Considerations for Design and Development", Clinical Pharmacokinetics, vol. 27, Issue 4, pp. 290-306.
Dvorak, H F., et al. (May 1995) "Vascular Permeability Factor/ Vascular Endothelial Growth Factor, Microvascular Hyperpermeability, and Angiogenesis", The American Journal of Pathology, vol. 146, No. 5, pp. 1029-1039.
Emmanouilides, et al. (May 30, 2007) "Front-line Bevacizumab in combination with Oxaliplatin, Leucovorin and 5-Fluorouracil (FOLFOX) in patients with metastatic colorectal cancer: a multi-center phase II study", Biomed Central Cancer, Article No. 91, pp. 1-7.
Eremina, Vera, et al. (Mar. 1, 2003) "Glomerular-Specific Alterations of VEGF—A Expression Lead to Distinct Congenital and Acquired Renal Diseases", Journal of Clinical Investigation, vol. 111, No. 5, pp. 707-716.
Fero, Olivier (Oct. 2004) "Targeting the Tumor Vascular Compartment to Improve Conventional Cancer Therapy", Trends in Pharmacological Sciences, vol. 25, Issue 10, pp. 536-542.
Ferrara, Napoleoen, et al. (May 1, 2004) "Discovery and Development of Bevacizumab, an Anti-VEGF Antibody for Treating Cancer", Nature Reviews Drug Discovery, vol. 3, pp. 391-400.
Ferrara, Napoleone (Oct. 2002) "VEGF and the Quest for Tumour Angiogenesis Factors", Nature Reviews Cancer, vol. 2, pp. 795-803.
Ferrara, Napoleone, et al. (2003) "The Biology of VEGF and its Receptors", Nature Medicine, vol. 9, No. 6, pp. 669-676.
Ferte, Charles, et al. (Feb. 17, 2009) "Wound Healing Delay After Central Venous Access Following DCF/VEGF-Trap Therapy", Investigational New Drugs, vol. 27, pp. 583-585.
Flyvbjerg, Allan, et al. (Oct. 2002) "Amelioration of Long-Term Renal Changes in Obese Type 2 Diabetic Mice by a Neutralizing Vascular Endothelial Growth Factor Antibody", Diabetes, vol. 51, No. 10, pp. 3090-3094.
Formica, Vincenzo (Feb. 2011) "Predictive Value of VEGF Gene Polymorphisms for Metastatic Colorectal Cancer Patients Receiving First-Line Treatment including Fluorouracil, Irinotecan, and Bevacizumab", International Journal of Colorectal Disease, vol. 26, Issue 2, pp. 143-151.
Formica, Vincenzo, et al. (Oct. 2009) "VEGF Polymorphisms as Predictors of Bevacizumab Efficacy in Metastatic Colorectal Cancer", European Journal of Cancer Supplements, vol. 7, No. 4, Abstract PP119, 17 Page.
Fraser, H M., et al. (Feb. 1, 2005) "Single Injections of Vascular Endothelial Growth Factor Trap Block Ovulation in the Macaque and Produce a Prolonged, Dose-Related Suppression of Ovarian Function", The Journal of Clinical Endocrinology & Metabolism, vol. 90, Issue 2, pp. 1114-1122.
Fuh, Germaine, et al. (May 1, 1998) "Requirements for Binding and Signaling of the Kinase Domain Receptor for Vascular Endothelial Growth Factor", Journal of Biological Chemistry, vol. 273, No. 18, pp. 11197-11204.
Gaya, Andrew, et al. (Aug. 2012) "A preclinical and Clinical Review of Aflibercept for the Management of Cancer", Cancer Treatment Reviews, vol. 38, Issue 5, pp. 484-493.
Gerber, Hans-Peter, et al. (Nov. 15, 2000) "Complete Inhibition of Rhabdomyosarcoma Xenograft Growth and Neovascularization Requires Blockade of Both Tumor and Host Vascular Endothelial Growth Factor", Cancer Research, vol. 60, Issue 22, pp. 6253-6258.
Glade-Bender, J, et al. (Apr. 2003) "VEGF Blocking Therapy in the Treatment of Cancer", Expert Opinion on Biological Therapy, vol. 3, No. 2, pp. 263-276.
Gotlieb, W H., et al. (Feb. 2012) "Intravenous Aflibercept for Treatment of Recurrent Symptomatic Malignant Ascites in Patients with Advanced Ovarian Cancer: A Phase 2, Randomised, Double-Blind, Placebo-Controlled Study", The Lancet Oncology, vol. 13, Issue 2, pp. 154-162.

(56) References Cited

OTHER PUBLICATIONS

Gramont, A DE., et al. (Sep. 21, 2016) "Randomized Trial Comparing Monthly Low-Dose Leucovorin and Fluorouracil Bolus with Bimonthly High-Dose Leucovorin and Fluorouracil Bolus Plus Continuous Infusion for Advanced Colorectal Cancer: a French Intergroup Study", Journal of Clinical Oncology, vol. 15, No. 2, pp. 808-815.

Groot, et al. (Jun. 1, 2011) "Myeloid Biomarkers Associated with Glioblastoma Response to Anti-Vascular Endothelial Growth Factor Therapy with Aflibercept", Clinical Cancer Research, vol. 17, Issue 14, pp. 4872-4881.

Hayashi, et al. (May 2014) "Biomarkers of Reactive Resistance and Early Disease Progression During Chemotherapy Plus Bevacizumab Treatment for Colorectal Carcinoma", Oncotarget, vol. 5, No. 9, pp. 2588-2595.

Heidaran, MA, et al. (Jan. 1995) "Beta PDGFR-IgG Chimera Demonstrates that Human Beta Pdgfr Ig-like Domains 1 to 3 are Sufficient for High Affinity PDGF BB Binding", The FASEB Journal, vol. 9, No. 1, pp. 140-145.

Heidaran, MA, et al. (Nov. 5, 1990) "Chimeric Alpha- and Beta-Platelet-Derived Growth Factor (PDGF) Receptors Define Three Immunoglobulin-Like Domains of the Alpha-PDGF Receptor that Determine PDGF-AA Binding Specificity", Journal of Biological Chemistry, vol. 265, No. 31, pp. 18741-18744.

Herbert Hurwitz, et al. (Jun. 3, 2004) "Bevacizumab plus Irinotecan, Fluorouracil, and Leucovorin for Metastatic Colorectal Cancer", The New England Journal of Medicine, vol. 350, No. 23, pp. 2335-2342.

Herley, et al. (Sep. 7, 1999) "Characterization of the VEGF Binding Site on the Flt-1 Receptor", Biochemical and Biophysical Research Communications, vol. 262, Issue 3, pp. 731-738.

Hileman, et al. (Dec. 6, 1998) "Glycosaminoglycan-protein interactions: definition of consensus sites in glycosaminoglycan binding proteins", BioEssays, vol. 20, Issue 2, pp. 156-167.

Hoff, Paulo M. (Feb. 2006) "A Phase I Study of Escalating Doses of the Tyrosine Kinase Inhibitor Semaxanib (SU5416) in Combination with Irinotecan in Patients with Advanced Colorectal Carcinoma", Japanese Journal of Clinical Oncology, vol. 36, Issue 2, pp. 100-103.

Holash, et al. (Aug. 20, 2002) "VEGF-Trap: A VEGF Blocker with Potent Antitumor Effects", Proceedings of the National Academy of Sciences of the United States of America, vol. 99, No. 17, pp. 11393-11398.

Hu, et al. (Nov. 2002) "Vascular Endothelial Growth Factor Immunoneutralization Plus Paclitaxel Markedly Reduces Tumor Burden and Ascites in Athymic Mouse Model of Ovarian Cancer", The American Journal of Pathology, vol. 161, Issue 5, pp. 1917-1924.

Hu, et al. (Oct. 2005) "Vascular Endothelial Growth Factor Trap Combined with Paclitaxel Strikingly Inhibits Tumor and Ascites, Prolonging Survival in a Human Ovarian Cancer Model", Clinical Cancer Research, vol. 11, Issue 19, pp. 6966-6971.

Huang, et al. (Jun. 24, 2003) "Regression of Established Tumors and Metastases by Potent Vascular Endothelial Growth Factor Blockade", Proceedings of the National Academy of Sciences of the United States of America, vol. 100, No. 13, pp. 7785-7790.

Hunt, et al. (May 1980) "Disorders of Wound Healing", World Journal of Surgery, vol. 4, No. 3, pp. 271-277.

Hwang, et al. (Dec. 4, 2004) "Irinotecan and 5-FU/Leucovorin in Metastatic Colorectal Cancer: Balancing Efficacy, Toxicity, and Logistics", Cancer Network, vol. 18, Issue 14, Supplement 14, pp. 26-34.

Ikehata, F, et al. (Jul. 15, 1998) "Autoantibodies Against CD38 (ADP-Ribosyl Cyclase/Cyclic ADP-Ribose Hydrolase) that Impair Glucose-Induced Insulin Secretion in Noninsulin-Dependent Diabetes Patients", Journal of Clinical Investigation, vol. 102, Issue 2, 395-401.

International Search Report and Written Opinion received for PCT Patent Application No. PCT/CN2013/085764, dated Apr. 3, 2014, 12 Pages.

International Search Report and Written Opinion received for PCT Patent Application No. PCT/EP2012/053026, dated Aug. 10, 2012, 24 Pages.

International Search Report and Written Opinion received for PCT Patent Application No. PCT/EP2012/057542, dated Jun. 19, 2012, 11 Pages.

International Search Report and Written Opinion received for PCT Patent Application No. PCT/EP2013/064079, dated Sep. 25, 2013, 10 Pages.

International Search Report and Written Opinion received for PCT Patent Application No. PCT/EP2013/066299, dated Oct. 30, 2013, 21 Pages.

International Search Report and Written Opinion received for PCT Patent Application No. PCT/EP2014/072731, dated Feb. 13, 2015, 10 Pages.

International Search Report and Written Opinion received for PCT Patent Application No. PCT/EP2015/066262, dated Aug. 24, 2015, 12 Pages.

International Search Report and Written Opinion received for PCT Patent Application No. PCT/FR2005/003005, dated May 3, 2006, 8 Pages.

International Search Report and Written Opinion received for PCT Patent Application No. PCT/FR2008/000943, dated Feb. 18, 2009, 12 Pages.

International Search Report and Written Opinion received for PCT Patent Application No. PCT/US2000/014142, dated Nov. 23, 2000, 4 Pages.

International Search Report and Written Opinion received for PCT Patent Application No. PCT/US2002/002466, dated Apr. 24, 2002, 2 Pages.

International Search Report and Written Opinion received for PCT Patent Application No. PCT/US2004/009246, dated Nov. 4, 2004, 11 Pages.

International Search Report and Written Opinion received for PCT Patent Application No. PCT/US2004/017721, dated Feb. 21, 2005, 7 Pages.

International Search Report and Written Opinion received for PCT Patent Application No. PCT/US2004/021059, dated Jul. 7, 2005, 7 Pages.

International Search Report and Written Opinion received for PCT Patent Application No. PCT/US2004/023815, dated Feb. 15, 2005, 14 Pages.

International Search Report and Written Opinion received for PCT Patent Application No. PCT/US2005/020762, dated Feb. 13, 2006, 11 Pages.

International Search Report and Written Opinion received for PCT Patent Application No. PCT/US2006/004557, dated Sep. 19, 2006, 12 Pages.

International Search Report and Written Opinion received for PCT Patent Application No. PCT/US2006/010600, dated Sep. 25, 2007, 7 Pages.

Isambert, et al. (Mar. 2012) "Phase I Dose-Escalation Study of Intravenous Aflibercept in Combination with Docetaxel in Patients with Advanced Solid Tumors", Clinical Cancer Research, vol. 18, Issue 6, pp. 1743-1750.

Jain, et al. (Sep. 2009) "The Role of Vascular Endothelial Growth Factor (VEGF) SNPs as Predictive and Prognostic Markers for Major Solid Tumors", Molecular Cancer Therapeutics, vol. 8, No. 9, pp. 2496-2508.

Jain, et al. (2006) "Lessons from Phase III Clinical Trials on anti-VEGF Therapy for Cancer", Nature Clinical Practice Oncology, vol. 3, No. 1, pp. 24-40.

Jain, et al. (Jun. 2009) "Biomarkers of Response and Resistance to Antiangiogenic Therapy", Nature Reviews Clinical Oncology, vol. 6, No. 6, pp. 327-338.

Jensen-Pippo, et al. (Jan. 1996) "Enteral Bioavailability of Human Granulocyte Colony Stimulating Factor Conjugated with Poly(Ethylene Glycol)", Pharmaceutical Research, vol. 13, No. 1, pp. 102-107.

Jin, et al. (Aug. 2010) "Aflibercept (VEGF Trap): One More Double-Edged Sword of anti-VEGF Therapy for Cancer", Clinical and Translational Oncology, vol. 12, No. 8, pp. 526-532.

Jones-Bolin, et al. (Jul. 2006) "The Effects of the Oral, Pan-VEGF-R Kinase Inhibitor CEP-7055 and Chemotherapy in Orthotopic

(56) References Cited

OTHER PUBLICATIONS

Models of Glioblastoma and Colon Carcinoma in Mice", Molecular Cancer Therapeutics, vol. 5, Issue 7, pp. 1744-1753.
Joulain, et al. (May 20, 2012) "Aflibercept Versus Placebo in Combination with FOLFIRI in Previously Treated Metastatic Colorectal Cancer (mCRC): Mean Overall Survival (OS) Estimation from a Phase III Trial (VELOUR)", Journal of Clinical Oncology, vol. 30, No. 15_supplement, Abstract 3602.
Juppner, H (Aug. 1995) "Functional Properties of the PTH/PTHrP Receptor", Bone, vol. 17, Issue 2, Supplement 1, pp. S39-S42.
Kabbinavar, et al. (Sep. 21, 2016) "Phase II, Randomized Trial Comparing Bevacizumab Plus Fluorouracil (FU)/Leucovorin (LV) With FU/LV Alone in Patients with Metastatic Colorectal Cancer", Journal of Clinical Oncology, Clinical Oncology, vol. 21, No. 1, pp. 60-65.
Kaklamani, et al. (Jan. 10, 2014) "Role of Capecitabine (Xeloda®) in Breast Cancer", Expert Review of Anticancer Therapy, vol. 3, Issue 2, pp. 137-144.
Katayama, et al. (Oct. 2004) "Retrospective Statistical Analysis of Lyophilized Protein Formulations of Progenipoietin using PLS: Determination of the Critical Parameters for Long-Term Storage Stability", Journal of Pharmaceutical Sciences, vol. 93, No. 10, pp. 2609-2623.
Kaufman, et al. (1999) "Transgenic Analysis of a 100-kb Human β-Globin Cluster-Containing DNA Fragment Propagated as a Bacterial Artificial Chromosome", Blood, vol. 94, pp. 3178-3184.
Kendall, et al. (Nov. 15, 1993) "Inhibition of Vascular Endothelial Cell Growth Factor Activity by an Endogenously Encoded Soluble Receptor", Proceedings of the National Academy of Sciences of the United States of America, vol. 90, No. 22, pp. 10705-10709.
Kendall, et al. (Sep. 13, 1996) "Identification of a Natural Soluble Form of the Vascular Endothelial Growth Factor Receptor, FLT-1, and Its Heterodimerization with KDR", Biochemical and Biophysical Research Communications, vol. 226, Issue 2, pp. 324-328.
Keyomarsi, et al. (Oct. 1986) "Folinic Acid Augmentation of the Effects of Fluoropyrimidines on Murine and Human Leukemic Cells", Cancer Research vol. 46, Issue 10, pp. 5229-5235.
Keyt, et al. (Mar. 8, 1996) "Identification of Vascular Endothelial Growth Factor Determinants for Binding KDR and FLT-1 Receptors", The Journal of Biological Chemistry, vol. 271, pp. 5638-5646.
Kim, et al. (Aug. 20, 2002) "Potent VEGF Blockade Causes Regression of Coopted Vessels in a Model of Neuroblastoma", Proceedings of the National Academy of Sciences of the United States of America, vol. 99, No. 17, pp. 11399-11404.
Konner, et al. (Oct. 2004) "Use of Soluble Recombinant Decoy Receptor Vascular Endothelial Growth Factor Trap (VEGF Trap) to Inhibit Vascular Endothelial Growth Factor Activity", Clinical Colorectal Cancer, vol. 4, Supplement 2, pp. S81-S85.
Kopetz, Scott (Dec. 14, 2009) "Phase II Trial of Infusional Fluorouracil, Irinotecan, and Bevacizumab for Metastatic Colorectal Cancer: Efficacy and Circulating Angiogenic Biomarkers Associated with Therapeutic Resistance", Journal of Clinical Oncology, vol. 28, No. 3, pp. 453-459.
Kurnianda, et al. (Jun. 5, 2009) "Elevation of Vascular Endothelial Growth Factor in Indonesian Advanced Stage Nasopharyngeal Carcinoma", Kobe Journal of Medical Sciences, vol. 55, No. 2 2009, pp. E36-E44.
Lambrechts, et al. (Sep. 10, 2015) "Evaluation of Efficacy and Safety Markers in a Phase II Study of Metastatic Colorectal Cancer Treated with Aflibercept in the First-Line Setting", British Journal of Cancer, vol. 113, No. 7, pp. 1027-1034.
Liu, et al. (Mar. 6, 2013) "Correlation of Angiogenic Biomarker Signatures with Clinical Outcomes in Metastatic Colorectal Cancer Patients Receiving Capecitabine, Oxaliplatin, and Bevacizumab", Cancer Medicine, vol. 2, Issue 2, pp. 234-242.
Lockhart, et al. (Jan. 10, 2010) "Phase I Study of Intravenous Vascular Endothelial Growth Factor Trap, Aflibercept, in Patients with Advanced Solid Tumors", Journal of Clinical Oncology, vol. 28, No. 2, pp. 207-214.

Loupakis, et al. (2009) "VEGF Gene Polymorphisms in the Prediction of Benefit from first-line FOLFIRI plus Bevacizumab (BV) in Metastatic Colorectal Cancer (mCRC) Patients (pts)", European Journal of Cancer. Supplement, vol. 7, No. 2, Abstract 6115, 357 Page.
Ludwig, et al. (Oct. 20, 2005) "Biomarkers in Cancer Staging, Prognosis and Treatment Selection", Nature Reviews Cancer, vol. 5, pp. 845-856.
Mahadevan, et al. (Nov. 17, 1995) "Structural Role of Extracellular Domain 1 of α-Platelet-derived Growth Factor (PDGF) Receptor for PDGF-AA and PDGF-BB Binding", The Journal of Biological Chemistry, vol. 270, pp. 27595-27600.
Maitland, et al. (May 2010) "Vascular Endothelial Growth Factor Pathway", Pharmacogenetics and Genomics, vol. 20, No. 5, pp. 346-349.
Mallone, et al. (Apr. 2001) "Autoantibody Response to CD38 in Caucasian Patients with Type 1 and Type 2 Diabetes", Diabetes, vol. 50, No. 4, pp. 752-762.
Mallone, et al. (Jul.-Aug. 2006) "Anti-CD38 Autoantibodies in Type? Diabetes", Diabetes/Metabolism Research and Reviews, vol. 22, No. 4, pp. 284-294.
Mantovani, et al. (1994) "Folate Binding Protein Distribution in Normal Tissues and Biological Fluids from ovarian carcinoma Patients as Detected by the Monoclonal Antibodies MOv18 and MOv19", European Journal of Cancer, vol. 30, Issue 3, 1994, pp. 363-369.
Maung, et al. (Feb. 2003) "Capecitabine/Bevacizumab Compared to Capecitabine Alone in Pretreated Metastatic Breast Cancer: Results of a Phase III Study", Clinical Breast Cancer, vol. 3, Issue 6, pp. 375-377.
Mayer, et al. (Jul. 2006) "Ratiometric Dosing of Anticancer Drug Combinations: Controlling Drug Ratios after Systemic Administration Regulates Therapeutic Activity in Tumor-Bearing Mice", Molecular Cancer Therapeutics, vol. 5, Issue 7, pp. 1854-1863.
Mettlin, et al. (Sep. 1, 1994) "Relative Sensitivity and Specificity of Serum Prostate Specific Antigen (PSA) Level Compared with Age-Referenced PSA, PSA Density, and PSA Change", Cancer, vol. 74, Issue 5, pp. 1615-1620.
Mi, et al. (May/Jun. 2002) "Effects of Polyethylene Glycol Molecular Weight and Concentration on Lactate Dehydrogenase Activity in Solution and After Freeze-thawing", PDA Journal of Pharmaceutical Science and Technology, vol. 56, pp. 115-123.
Morton, Lori (2014) "Control of Hypertension Induced by Anti-VEGF Trap Therapy with Antihypertensive Drugs", Regeneron Pharmaceuticals, Inc., document filed during examination of EP06720549.2, pp. 1-14.
Ngo, et al. (1994) "Computational complexity, protein structure prediction, and the Levinthal paradox,", In "The Protein Folding Problem and Tertiary Structure Prediction" Kenneth Merz, Jr. and Scott LeGrand, eds., pp. 1-82.
Nickoloff, et al. (Jul. 1999) "Injection of Pre-Psoriatic Skin with CD4+ T Cells Induces Psoriasis", vol. 155, No. 1, pp. 145-158.
Nickoloff, et al. (Sep. 1999) "The Immunologic and Genetic Basis of Psoriasis", Archives of Dermatological Research, vol. 135, No. 9, pp. 1104-1110.
Palu, et al. (Mar. 1999) "In Pursuit of New Developments for Gene Therapy of Human Diseases", Journal of Biotechnology, vol. 68, No. 1, pp. 1-13.
Park, et al. (Oct. 14, 1994) "Placenta growth factor: Potentiation of Vascular Endothelial Growth Factor Bioactivity, in Vitro and in Vivo, and High Affinity Binding to Flt-1 but not to Flk-1/KDR", Journal of Biological Chemistry, vol. 269, No. 41, pp. 25646-25654.
Pasqualetti, et al. (Dec. 22, 2006) "Vascular Endothelial Growth Factor Pharmacogenetics: A New Perspective for Anti-Angiogenic Therapy", Pharmacogenomics, vol. 8, No. 1, pp. pp. 49-66.
Pepe, et al. (Jul. 18, 2001) "Phases of Biomarker Development for Early Detection of Cancer", Journal of the National Cancer Institute, vol. 93, Issue 14, pp. 1054-1061.
Pettit, et al. (Dec. 1, 1998) "The Development of Site-Specific Drug-Delivery Systems for Protein and Peptide Biopharmaceuticals", Trends in Biotechnology, vol. 16, Issue 8, pp. 343-349.

(56) References Cited

OTHER PUBLICATIONS

Phillips, et al. (2001) "The Challenge of Gene Therapy and DNA Delivery", Journal of Pharmacy and Pharmacology, vol. 53, No. 9, pp. 1169-1174.
Poon, et al. (Sep. 21, 2016) "Clinical Implications of Circulating Angiogenic Factors in Cancer Patients", Journal of Clinical Oncology, vol. 19, No. 4, pp. 1207-1225.
Reinacher-Schick, et al. (2008) "Drug Insight: Antiangiogenic Therapies for Gastrointestinal Cancers—Focus on Monoclonal Antibodies", Nature Clinical Practice Gastroenterology & Hepatology, vol. 5, pp. 250-267.
Rixe, et al. (Dec. 12, 2016.) "Safety and Pharmacokinetics of Intravenous VEGF Trap Plus Irinotecan, 5-Fluorouracil, and Leucovorin (I-LV5FU2) in a Combination Phase I Clinical Trial of Patients with Advanced Solid Tumors", Journal of Clinical Oncology, vol. 24, No. 18_supplement, Abstract 13161.
Rixe, et al. (May 20, 2008) "A Phase I Dose Escalation (DE) and Pharmacokinetics (PK) Study of Intravenous Aflibercept (VEGF Trap) Plus Irinotecan, 5-Fluorouracil, and Leucovorin (I-LV5FU2) in Patients with Advanced Solid Tumors (STs)", Journal of Clinical Oncology, vol. 26, No. 15, supplement, Abstract 3557.
Rudge, et al. (Nov. 20, 2007) "VEGF Trap Complex Formation Measures Production Rates of VEGF, providing a Biomarker for Predicting Efficacious Angiogenic Blockade", Proceedings of the National Academy of Sciences of the United States of America, vol. 104, No. 47, pp. 18363-18370.
Rudikoff, et al. (Mar. 1, 1982) "Single Amino Acid Substitution Altering Antigen-Binding Specificity", Proceedings of the National Academy of Sciences of the United States of America, vol. 79, pp. 1979-1983.
Saltz, et al. (Dec. 3, 2000) "Irinotecan-Based Combinations for the Adjuvant Treatment of Stage III Colon Cancer", Oncology, vol. 14, Supplement 14, pp. 47-50.
Ji, et al. (Apr. 1, 2005) "Phase II Study of Irinotecan, 5-Fluorouracil and Leucovorin as First-line Therapy for Advanced Colorectal Cancer", Japanese Journal of Clinical Oncology, vol. 35, Issue 4, pp. 214-217.
Sanofi (Jan. 13, 2015) "A Study of Intravenous Aflibercept With Docetaxel in Chinese Patients with Solid Tumors", ClinicalTrials. gov Identifier: NCT01148615.
Sanofi (Jul. 26, 2012) "Aflibercept Versus Placebo in Combination with Irinotecan and 5-FU in the Treatment of Patients with Metastatic Colorectal Cancer After Failure of an Oxaliplatin Based Regimen (VELOUR)", ClinicalTrials.gov Identifier: NCT00561470, 4 Page.
Sanofi (Jun. 3, 2016) "VEGF Trap in Treating Patients with Solid Tumors or Non-Hodgkin's Lymphoma", ClinicalTrials.gov Identifier: NCT00045266, 8 Pages.
Sanofi-Aventis U.S. LLC (Sep. 2014) "Starting Therapy with Zaltrap. A Guide for Patients and Caregivers", 14 Pages.
Schneider, et al. (Oct. 1, 2008) "Association of Vascular Endothelial Growth Factor and Vascular Endothelial Growth Factor Receptor-2 Genetic Polymorphisms with Outcome in a Trial of Paclitaxel Compared with Paclitaxel Plus Bevacizumab in Advanced Breast Cancer: ECOG 2100", Journal of Clinical Oncology, vol. 26, No. 28, pp. 4672-4678.
Semela, et al. (Nov. 2004) "Angiogenesis and Hepatocellular Carcinoma", Journal of Hepatology, vol. 41, Issue 5, pp. 864-880.
Sharifi, et al. (Dec. 1998) "Improving Monoclonal Antibody Pharmacokinetics via Chemical Modification", The Quarterly Journal of Nuclear Medicine and Molecular, vol. 42, No. 4, pp. 242-249.
Shibuya, et al. (Apr. 1, 1990) "Nucleotide Sequence and Expression of a Novel Human Receptor-type Tyrosine Kinase Gene (flt) Closely Related to the fms Family", Oncogene, vol. 5, No. 4, pp. 519-524.
Skolnick, et al. (Jan. 1, 2000,) "From Genes to Protein Structure and Function: Novel Applications of computational approaches in the Genomic Era", Trends in Biotechnology, vol. 18, Issue 1, pp. 34-39.
Smerdel, et al. (Aug. 1, 2010) "The predictive value of serum VEGF in multiresistant ovarian cancer patients treated with bevacizumab", Gynecologic Oncology, vol. 118, Issue 2, pp. 167-171.
Smith, et al. (1997) "The Challenges of Genome Sequence Annotation or "The devil is in the details",", Nature Biotechnology, vol. 15, pp. 1222-1223.
Stewart, et al. (Jul. 26, 2012) "Clinical and Differential Utility of VEGF Inhibitors in Wet Age-Related Macular Degeneration: Focus on Aflibercept", Clinical Ophthalmology, vol. 6, pp. 1175-1186.
Stone, et al. (May 2010) "Collateral Damage: Toxic Effects of Targeted Antiangiogenic Therapies in Ovarian Cancer", The Lancet Oncology, vol. 11, Issue 5, pp. 465-475.
Suri, Chitra (Oct. 16, 1998) "Increased Vascularization in Mice Overexpressing Angiopoietin-1", Science, vol. 282, No. 5388, pp. 468-471.
Tabernero, et al. (Sep. 2011) "Results From VELOUR, a Phase 3 Study of Aflibercept (A) Versus Placebo (pbo) in Combination with FOLFIRI for the Treatment of Patients (pt) with Previously Treated Metastatic Colorectal Cancer (MCRC)", European Journal of Cancer, vol. 47, Supplement 2, Abstract 6LBA, 5 Page.
Tanaka, et al. (Nov. 21, 1995) "Characterization of the Ligand Binding Domain of FKT-1", The 8th Annual Meeting of Japanese Molecular Biology, Abstract 2P-227.
Tanaka, et al. (Sep. 1997) "Characterization of the Extracellular Domain in Vascular Endothelial Growth Factor Receptor-1 (Flt-1 Tyrosine Kinase)", Japanese Journal of Cancer Research, vol. 88, No. 9, pp. 867-876.
Tang, et al. (May 2008) "Phase II Trial of Aflibercept (VEGF Trap) in Previously Treated Patients with Metastatic Colorectal Cancer (MCRC): A PMH Phase II Consortium Trial", Journal of Clinical Oncology, vol. 26, No. 15 supplement, Abstract 4027.
Tang, et al. (Nov. 2012) "Phase II Clinical and Pharmacokinetic Study of Aflibercept in Patients with Previously Treated Metastatic Colorectal Cancer", Clinical Cancer Research, vol. 18, Issue 21, pp. 6023-6031.
Tate, et al. (Feb. 17, 2003) "Comparison of Seven Different Heterologous Protein Expression Systems for the Production of the Serotonin Transporter", Biochimica et Biophysica Acta (BBA)—Biomembranes, vol. 1610, Issue 1, pp. 141-153.
Teng, et al. (Sep. 2010) "Clinical Applications of VEGF-Trap (Aflibercept) in Cancer Treatment", Journal of the Chinese Medical Association, vol. 73, Issue 9, pp. 449-456.
Terman, et al. (Sep. 30, 1992) "Identification of the KDR Tyrosine Kinase as a Receptor for Vascular Endothelial Cell Growth Factor", Biochemical and Biophysical Research Communications, vol. 187, Issue 3, pp. 1579-1586.
Terman, et al. (Sep. 1, 1991) "Identification of a New Endothelial Cell Growth Factor Receptor Tyrosine Kinase", Oncogene vol. 6, No. 9, pp. 1677-1683.
Tew, et al. (Dec. 22, 2009) "Phase 1 Study of Aflibercept Administered Subcutaneously to Patients with Advanced Solid Tumors", Clinical Cancer Research, vol. 16, No. 1, pp. 358-366.
Thomas, et al. (2013) "Clinical Experience with Aflibercept in Metastatic Colorectal Cancer (mCRC): A Single Institution Experience", NCRI Cancer Conferences, Abstract LB82.
Tiilikainen, et al. (Feb. 1980) "Psoriasis and HLA-Cw6", British Journal of Dermatology, vol. 102, Issue 2, pp. 179-184.
Tischer, et al. (Jun. 25, 1991) "The Human Gene for Vascular Endothelial Growth Factor. Multiple Protein Forms are Encoded Through Alternative Exon Splicing", The Journal of Biological Chemistry, vol. 266, pp. 11947-11954.
Tokuriki, et al. (Oct. 2009) "Stability Effects of Mutations and Protein Evolvability", Current Opinion in Structural Biology, vol. 19, Issue 5, pp. 596-604.
Tournigand, et al. (Sep. 21, 2016) "FOLFIRI Followed by FOLFOX6 or the Reverse Sequence in Advanced Colorectal Cancer: A Randomized GERCOR Study", Journal of Clinical Oncology, vol. 22, No. 2, pp. 229-237.
Tsutsumi, et al. (Jan. 1997) "PEGylation of Interleukin-6 Effectively Increases its Thrombopoietic Potency", Thrombosis and Haemostasis, vol. 77, No. 1, pp. 168-173.
Vanhoefer, et al. (Jun. 2004) "Irinotecan in Combination with New Agents", European Journal of Cancer Supplements, vol. 2, Issue 7, pp. 14-20.
Verslype, et al. (Dec. 12, 2016) "Validation of the selected dose of aflibercept (VEGF Trap) plus irinotecan, 5-fluorouracil, and leucovorin

(56) References Cited

OTHER PUBLICATIONS (I-LV5FU2) in a phase I clinical trial of patients (pts) with advanced solid tumors (STs): Preliminary results", Journal of Clinical Oncology, vol. 26, No. 15 supplement, Abstract 14540.
Vredenburgh, et al. (Feb. 2007) "Phase II Trial of Bevacizumab and Irinotecan in Recurrent Malignant Glioma", Clinical Cancer Research, vol. 13, Issue 4, pp. 1253-1257.
Wang, et al. (Dec. 1, 1999) "Rapid analysis of gene expression (RAGE) facilitates universal expression profiling", Nucleic Acids Research, vol. 27, No. 23, pp. 4609-4618.
Wang, et al. (Jan. 4, 2012) "Aflibercept in the Treatment of Metastatic Colorectal Cancer", Clinical Medicine Insights: Oncology, vol. 6, pp. 19-30.
Wang, Wei (Aug. 20, 1999) "Instability, Stabilization and Formulation of Liquid Protein Pharmaceuticals", International Journal of Pharmaceutics, vol. 185, Issue 2, pp. 129-188.
Warner, et al. (Sep. 1, 1999) "Enhancing Therapeutic Glycoprotein Production in Chinese Hamster Ovary Cells by Metabolic Engineering Endogenous Gene Control with Antisense DNA and Gene Targeting", Glycobiology, vol. 9, Issue 9, pp. 841-850.
Webb, et al. (Feb. 1, 2002) "A new mechanism for decreasing aggregation of Recombinant Human Interferon-Y by a Surfactant: Slowed Dissolution of Lyophilized Formulations in a Solution Containing 0.03% Polysorbate 20", Journal of pharmaceutical sciences, vol. 91, No. 2, pp. 543-558.
Wehland, et al. (2013 May) "Biomarkers for Anti-Angiogenic Therapy in Cancer", International Journal of Molecular Sciences, vol. 14, No. 5, pp. 9338-9364.
Wells, et al. (Sep. 18, 1990) "Additivity of Mutational Effects in Proteins", Biochemistry, vol. 29, No. 37, pp. 8509-8517.
Wiesmann, et al. (Nov. 28, 1997) "Crystal Structure at 1.7 Å Resolution of VEGF in Complex with Domain 2 of the Flt-1 Receptor", Cell, vol. 91, Issue 5, pp. 695-704.
Wigley, (1994) "Site-Specific Transgene Insertion: An Approach", Reproduction, Fertility and Development, vol. 6, No. 5, pp. 585-588.
Witmer, et al. (Jan. 2003) "Vascular Endothelial Growth Factors and Angiogenesis in Eye Disease", Progress in Retinal and Eye Research, vol. 22, Issue 1, pp. 1-29.
Wong, et al. (Jun. 19, 2001) "Excessive Tumor-Elaborated VEGF and its Neutralization Define a Lethal Paraneoplastic Syndrome", Proceedings of the National Academy of Sciences of the United States of America, vol. 98, No. 13, pp. 7481-7486.
Wormald, et al. (Jul. 15, 1999) "Glycoproteins: Glycan Presentation and Protein-Fold Stability", Structure, vol. 7, Issue 7, pp. R155-R160.
Wrone-Smith, et al. (Oct. 15, 1996) "Dermal Injection of Immunocytes Induces Psoriasis", Journal of Clinical Investigation, vol. 98, No. 8, pp. 1878-1887.
Wulff, et al. (Jul. 1, 2002) "Prevention of Thecal Angiogenesis, Antral Follicular Growth, and Ovulation in the Primate by Treatment with Vascular Endothelial Growth Factor Trap R1 R2", Endocrinology, vol. 143, Issue 7, pp. 2797-2807.
Yamazaki, et al. (Sep. 22, 2016) "Phase I Dose Escalation and Pharmacokinetics Study of Intravenous Aflibercept Plus Irinotecan, 5-Fluorouracil, and Folinic Acid (FOLFIRI) in Patients with Metastatic Colorectal Cancer", Journal of Clinical Oncology, vol. 29, No. 4, supplement, Abstract 538.
Yang, et al. (2007) "Progress in the treatment of colorectal cancer", Oncology Progress, vol. 5, No. 2, pp. 143-150.
Yang, et al. (Aug. 15, 1995) "The use of Polyethylene Glycol-Modified Interleukin-2 (PEG-IL-2) in the Treatment of Patients with Metastatic Renal Cell Carcinoma and Melanoma. A Phase I Study and a Randomized Prospective Study Comparing IL-2 Alone Versus IL-2 Combined with PEG-IL-2", Cancer, vol. 76, No. 4, pp. 687-694.
Yazici MD, et al. (Dec. 2005) "Antivascular Therapy of Oral Tongue Squamous Cell Carcinoma with PTK787", The Laryngoscope, vol. 115, Issue 12, pp. 2249-2255.

Yokoi, et al. (May 1, 2005) "Dual Inhibition of Epidermal Growth Factor Receptor and Vascular Endothelial Growth Factor Receptor Phosphorylation by AEE788 Reduces Growth and Metastasis of Human Colon Carcinoma in an Orthotopic Nude Mouse Model", Cancer Research, vol. 65, Issue 9, pp. 3716-3725.
Yu, et al. (Apr. 8, 1994) "Structural Coincidence of Alpha PDGFR Epitopes Binding to Platelet-Derived Growth Factor-Aa and a Potent Neutralizing Monoclonal Antibody", The Journal of Biological Chemistry, vol. 269, No. 14, pp. 10668-10674.
Yu, et al. (Mar. 31, 1995) "Differential Requirement of a Motif within the Carboxyl-terminal Domain of α-Platelet-derived Growth Factor (αPDGF) Receptor for PDGF Focus Forming Activity Chemotaxis, or Growth", The Journal of Biological Chemistry, vol. 270, No. 13, pp. 7033-7036.
Zehetner, et al. (May 2015) "Systemic Counterregulatory Response of Placental Growth Factor Levels to Intravitreal Aflibercept Therapy", Investigative Ophthalmology & Visual Science, vol. 56, Issue 5, pp. 3279-3286.
Zimmermann, et al. (Jan. 2007) "Multi-Target Therapeutics: when the Whole is Greater than the Sum of the Parts", Drug Discovery Today, vol. 12, Issues 1-2, pp. 34-42.
U.S. Appl. No. 14/000,942 / 2013/0330341, filed Aug. 22, 2013 / Dec. 12, 2013, Marielle Chiron-Blondel.
U.S. Appl. No. 15/409,377 / 2018/0078496, filed Jan. 18, 2017 / Mar. 22, 2018, Sylvie Assadourian.
U.S. Appl. No. 15/408,827 / 2017 2017/012387 / U.S. Pat. No. 10,501,523, filed Jan. 18, 2017 / May 4, 2017 / Dec. 10, 2019, Marielle Chiron-Blondel.
U.S. Appl. No. 15/414,722 / 2018/0113134, filed Jan. 25, 2017 / Apr. 26, 2018, Jennifer Dreymann.
"Zaltrap Marketing Authorization", Issued by European Commission (2013).
Cersosimo, Robert J. (Dec. 1, 1998) "Irinotecan: A New Antineoplastic Agent for the Management of Colorectal Cancer", Annals of Pharmacotherapy, vol. 32, Issue 12, pp. 1324-1333.
Cunningham, et al. (Aug. 2001) "Optimizing the Use of Irinotecan in Colorectal Cancer", The Oncologist, vol. 6, Supplement 4, pp. 17-23.
Dowlati, et al. (Mar. 2008) "Cell Adhesion Molecules, Vascular Endothelial Growth Factor, and Basic Fibroblast Growth Factor in Patients with Non-Small Cell Lung Cancer Treated with Chemotherapy with or without Bevacizumab—an Eastern Cooperative Oncology Group Study", Clinical Cancer Research, vol. 14, Issue 5, pp. 1407-1412.
Horn, et al. (Oct. 13, 2009) "Phase II Study of Cisplatin Plus Etoposide and Bevacizumab for Previously Untreated, Extensive-Stage Small-Cell Lung Cancer: Eastern Cooperative Oncology Group Study E3501", Journal of Clinical Oncology, vol. 27, No. 35, pp. 6006-6011.
International Preliminary Report on Patentability corresponding to International Patent Application No. PCT/US2000/014142, completed Aug. 30, 2001.
International Preliminary Report on Patentability corresponding to International Patent Application No. PCT/US2002/002466, completed Apr. 16, 2003.
International Preliminary Report on Patentability corresponding to International Patent Application No. PCT/US2004/009246, completed Apr. 28, 2008.
International Preliminary Report on Patentability corresponding to International Patent Application No. PCT/US2004/017721, completed Mar. 6, 2006.
International Preliminary Report on Patentability corresponding to International Patent Application No. PCT/US2004/021059, completed Jul. 10, 2006.
International Preliminary Report on Patentability corresponding to International Patent Application No. PCT/US2004/023815, completed Nov. 29, 2005.
International Search Report and Written Opinion received for PCT Patent Application No. PCT/EP2017/051363, mailed on May 19, 2017, 16 pages.
Invitrogen Corporation (Aug. 11, 2008) "Technical Resources-Media Formulations: Hank's Balanced Salt Solution (Hbss) (1X) liquid", 1 Page.

(56) References Cited

OTHER PUBLICATIONS

Motzer, et al. (Dec. 12, 2016.) "Phase III Randomized Trial of Sunitinib Malate (SU11248) Versus Interferon-Alfa (IFN-a) as First-Line Systemic Therapy for Patients with Metastatic Renal Cell Carcinoma (mRCC)", Journal of Clinical Oncology, vol. 24, No. 18_Supplement.

Reagan-Shaw, et al. (Mar. 2008) "Dose Translation from Animal to Human Studies Revisited", FASEB Journal, vol. 22, No. 3, pp. 659-661.

SANOFI (Feb. 17, 2011) "Aflibercept Versus Placebo in Combination with Irinotecan and 5-FU in the Treatment of Patients with Metastatic Colorectal Cancer After Failure of an Oxaliplatin Based Regimen (VELOUR)", ClinicalTrials.gov Identifier: NCT00561470, 25 Pages.

* cited by examiner

SEQUENCE LISTING

<160> NUMBER OF SEQ ID NOS: 2

<210> SEQ ID NO 1
<211> LENGTH: 431
<212> TYPE: PRT
<213> ORGANISM: Artificial Sequence
<220> FEATURE:
<223> OTHER INFORMATION: Aflibercept

<400> SEQUENCE: 1

Ser Asp Thr Gly Arg Pro Phe Val Glu Met Tyr Ser Glu Ile Pro Glu
1               5                   10                  15

```
Ile Ile His Met Thr Glu Gly Arg Glu Leu Val Ile Pro Cys Arg Val
                20                  25                  30

Thr Ser Pro Asn Ile Thr Val Thr Leu Lys Lys Phe Pro Leu Asp Thr
            35                  40                  45

Leu Ile Pro Asp Gly Lys Arg Ile Ile Trp Asp Ser Arg Lys Gly Phe
        50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Asp Lys Thr
        195                 200                 205

His Thr Cys Pro Pro Cys Pro Ala Pro Glu Leu Leu Gly Gly Pro Ser
210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
            260                 265                 270

Lys Thr Lys Pro Arg Glu Glu Gln Tyr Asn Ser Thr Tyr Arg Val Val
        275                 280                 285

Ser Val Leu Thr Val Leu His Gln Asp Trp Leu Asn Gly Lys Glu Tyr
    290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
                325                 330                 335

Pro Pro Ser Arg Asp Glu Leu Thr Lys Asn Gln Val Ser Leu Thr Cys
            340                 345                 350

Leu Val Lys Gly Phe Tyr Pro Ser Asp Ile Ala Val Glu Trp Glu Ser
        355                 360                 365

Asn Gly Gln Pro Glu Asn Asn Tyr Lys Thr Thr Pro Pro Val Leu Asp
    370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
                405                 410                 415

Leu His Asn His Tyr Thr Gln Lys Ser Leu Ser Leu Ser Pro Gly
            420                 425                 430
```

```
<210> SEQ ID NO 2
<211> LENGTH: 99
<212> TYPE: PRT
<213> ORGANISM: Homo sapiens

<400> SEQUENCE: 2

Met Thr Ser Lys Leu Ala Val Ala Leu Leu Ala Ala Phe Leu Ile Ser
1               5                  10                  15

Ala Ala Leu Cys Glu Gly Ala Val Leu Pro Arg Ser Ala Lys Glu Leu
            20                  25                  30

Arg Cys Gln Cys Ile Lys Thr Tyr Ser Lys Pro Phe His Pro Lys Phe
            35                  40                  45

Ile Lys Glu Leu Arg Val Ile Glu Ser Gly Pro His Cys Ala Asn Thr
    50                  55                  60

Glu Ile Ile Val Lys Leu Ser Asp Gly Arg Glu Leu Cys Leu Asp Pro
65                  70                  75                  80

Lys Glu Asn Trp Val Gln Arg Val Val Glu Lys Phe Leu Lys Arg Ala
                85                  90                  95

Glu Asn Ser
```

METHOD FOR PREDICTING THE OUTCOME OF A TREATMENT WITH AFLIBERCEPT OF A PATIENT SUSPECTED TO SUFFER FROM A CANCER

CROSS-REFERENCE TO RELATED APPLICATIONS

This application is a divisional of U.S. patent application Ser. No. 15/408,827, filed Jan. 18, 2017, which is a continuation of International Patent Application No. PCT/EP2015/066262, filed Jul. 16, 2015, which claims priority to European Patent Application No. 14306172.9, filed Jul. 18, 2014, the entire disclosures of which are hereby incorporated herein by reference.

BACKGROUND OF THE INVENTION

Field of the Invention

The present invention concerns the use of interleukin 8 (IL8) as a biomarker for predicting the outcome of the treatment with aflibercept, or ziv-aflibercept, of a patient suspected to suffer from cancer.

Aflibercept, or ziv-aflibercept, also referred to as VEGFR1R2-Fc.DELTA.C1 Flt1D2.Flk1D3.Fc.DELTA.C1 or AVE0005, is a homo dimer protein, with each dimer comprising two identical monomers, each of which is a fusion protein comprising the signal sequence of VEGFR1 fused to the D2 Ig domain of the VEGFR1 receptor, itself fused to the D3 Ig domain of the VEGFR2 receptor, in turn fused to the Fc domain of IgG1.

The protein chain is glycosylated, with N-acetyl-glucosamine, fucose, galactose, mannose and sialic acids contributing to the carbohydrate structures. The N-linked oligosaccharides consist of mainly bi-antennary structures with zero, one or two terminal sialic acids. The monomer has the amino acid sequence SEQ ID No 1.

The U.S. Food and Drug Administration (FDA) already approved aflibercept under the trade name EYLEA® for the treatment of patients with neovascular (wet) age-related macular degeneration (AMD). In particular, EYLEA® is the trade name for aflibercept as generated, processed and formulated for intravitreal injection.

At the time of registration of aflibercept (zaltraP) for cancer indication, and In light of aflibercept's approved use in treating AMD, the FDA requested that a different name (ziv-aflibercept) be given for the compound's use in the treatment of cancer. Thus, ziv-aflibercept is the United States Adopted Name (USAN) accepted by FDA to designate a pharmaceutical composition comprising aflibercept as generated, processed and formulated for injection via intravenous infusion. Ziv-aflibercept has been approved by the FDA for sale under the tradename ZALTRAP® for the treatment of metastatic colorectal cancer (mCRC).

The European Medicines Agency (EMA) approved zaltrap as well however did not request separate names for the compound. Thus, in the European Union the name "aflibercept" is used regardless of the indication.

ZALTRAP® and EYLEA® are obtained by slightly different processes. They both contain aflibercept or ziv-aflibercept, but the ratio of aggregates of aflibercept or ziv-aflibercept is slightly different in ZALTRAP® and EYLEA®.

ZALTRAP® approval was based on data obtained from the VELOUR trial—a multicenter, randomized, placebo-controlled phase III trial, which compared the efficacy of aflibercept versus placebo in combination with the FOLFIRI regimen for patients with mCRC previously treated with an oxaliplatin containing regimen.

AFFIRM, an open-label, non-comparative, phase II study, was conducted to assess the combination of aflibercept and modified FOLFOX6 (mFOLFOX6) given as first-line therapy in patients with mCRC. The primary endpoint was 12-month progression-free survival (PFS) whereas exploration of biomarkers was among the secondary objectives.

In an attempt to understand the key factors associated with aflibercept efficacy and safety, an investigation assessing biomarkers for aflibercept treatment in prospectively collected, tumor tissues and serially sampled plasma from patients participating in the AFFIRM study was conducted.

Plasma proteins and genetic variants, representing either single nucleotide polymorphisms (SNPs) in angiogenicpathway genes or somatic mutations in key oncogenic drivers of mCRC, were analyzed to assess if they could predict response to aflibercept with respect to PFS. Subsequently, one also assessed whether any of these markers correlated with anti-angiogenic drug-induced AEs, such as gastrointestinal perforation, thrombosis, hypertension and proteinuria.

Despites the efficacy and the safety of the treatment of cancer by aflibercept it remains a goal to better identify patients who should benefit more from the treatment.

It has now been discovered that high IL8 levels at baseline correlated with shorter survival times, and patients with increasing levels of IL8 during treatment were more likely to progress. This suggests that patients with high IL8 levels, at baseline or during treatment, are at increased risk of disease progression during aflibercept therapy.

The role of IL8-in tumor development and progression is suggested in the prior art In a phase II trial hepatocellular carcinoma patients received bevacizumab (Boige V, Malka D, Bourredjem A et al. Efficacy, safety, and biomarkers of single-agent bevacizumab therapy in patients with advanced hepatocellular carcinoma. Oncologist 2012; 17: 1063-1072). Circulating endothelial cells (CECs) and plasma cytokines and angiogenic factors (CAFs) were measured at baseline and throughout treatment.

This study showed that elevated baseline IL-8 (above 80 pg/ml) and IL-6 levels were correlated with both a shorter progression-free survival (PFS) interval and a shorter overall survival (OS) time.

However the authors cite another study with sorafenib wherein conversely, IL-8 was the only serum cytokine not correlated with the PFS outcome.

In another phase II trial metastatic colorectal cancer (mCRC) patients received bevacizumab (Kopetz S, Hoff P M, Morris J S et al. Phase II trial of infusional fluorouracil, irinotecan, and bevacizumab for metastatic colorectal cancer: efficacy and circulating angiogenic biomarkers associated with therapeutic resistance. J Clin Oncol 2010; 28: 453-459).

Levels of 37 CAFs were assessed at baseline, during treatment, and at the time of progressive disease (PD).

The authors conclude that elevated baseline IL8 above the median value of 3.7 pg/ml was associated with shorter PFS times.

These results were obtained with bevacizumab which is an antibody. Aflibercept is not an antibody but a fusion protein and thus has a different mode of action.

It is not possible to predict the effect of a biomarker on the efficiency of cancer treatment by a given drug from results obtained with another drug.

A fortiori the threshold above or under which a patient is considered as a candidate for treatment cannot be extrapolated between two different drugs.

BRIEF SUMMARY OF THE INVENTION

The invention relates to the use of interleukin-8 (IL-8) as a biomarker for predicting the outcome of the treatment with aflibercept, or ziv-aflibercept of a patient suspected to suffer from a cancer.

In one aspect, the present invention provides a method of determining whether a patient suspected to suffer from cancer is a candidate for aflibercept, or ziv-aflibercept therapy for the said cancer comprising the step of subjecting a patient's biological sample to at least one assay to measure at baseline the IL-8 level, wherein when the biological sample IL-8 level is low relative to a reference level of expression of IL-8, the patient is identified as a candidate for therapy for cancer.

In another aspect, the present invention provides a method of determining whether a patient suspected to suffer from cancer is a candidate for aflibercept, or ziv-aflibercept therapy for the said cancer comprising the step of subjecting a patient's biological sample to at least one assay to measure at baseline the IL-8 level, wherein when the biological sample IL-8 level is high relative to a reference level of expression of IL-8, the patient is identified as not being a candidate for therapy for cancer.

In an embodiment the reference level of expression of IL-8 is comprised between around 10 and around 30 pg/ml.

In a further embodiment the reference level of expression of IL-8 is comprised between around 15 and around 25 pg/ml or around 17 and around 21 pg/ml.

In a further embodiment the reference level of expression of IL-8 is around 18 pg/ml, around 19 pg/ml or around 20 pg/ml.

The invention relates also to a method for treating a patient with a cancer with aflibercept, or ziv-aflibercept, comprising administering a therapeutically effective amount of aflibercept, or ziv-aflibercept to the patient, wherein the IL-8 level in the patient's biological sample is low relative to a reference level of expression of IL-8.

The invention further relates to a method of optimizing therapeutic efficacy for treatment of a cancer, comprising the steps of:
  a) administering aflibercept, or ziv-aflibercept to a patient suspected to suffer from a cancer; and
  b) determining the level of interleukin-8 (IL-8) in patient's biological sample,
wherein an increase of the interleukin-8 (IL-8) level indicates the need to decrease the amount of aflibercept, or ziv-aflibercept in subsequent administrations.

A further object of the invention is a method of managing the risk to allow a safe use of aflibercept, or ziv-aflibercept in the treatment of a patient suspected to suffer from a cancer, said method comprising the following steps:
  a) before beginning of the treatment with aflibercept, or ziv-aflibercept, determining the interleukin-8 (IL-8) level in a biological sample from the patient;
  b) along the treatment determining the interleukin-8 (IL-8) level in a biological sample from the patient
  c) comparing the interleukin-8 (IL-8) level determined in step (b) with the level determined in step (a),
whereby a higher interleukin-8 (IL-8) level in the sample of step (b) compared to that of level in the sample of step (a) indicates that the patient should be closely monitored.

In an embodiment of one of the methods described above the biological sample is chosen from the group consisting of blood, serum and plasma.

In an embodiment of one of the methods described above the cancer is a colon cancer, a colorectal cancer or a rectal cancer.

In a further embodiment of one of the the colorectal cancer is a metastatic colorectal cancer.

In another embodiment of the invention, the subject is treated with aflibercept and further undergoes a chemotherapeutic treatment with oxaliplatin, 5-fluorouracil (5-FU) and folinic acid (i.e. the FOLFOX treatment), folinic acid, 5-fluorouracil and irinotecan (i.e. the FOLFIRI treatment), or 5-fluorouracil and folinic acid (i.e. the FUFOL or LV5FU2 treatment).

The chemotherapeutic treatment may combine at least 2, 3, 4, 5, 6, 7, 8, 9, 10 or at most 10, 9, 8, 7, 6, 5, 4, 3, 2 agents, such as e.g. a combination of oxaliplatin, 5-fluorouracil (5-FU) and folinic acid (i.e. the FOLFOX treatment or the modified FOLFOX6 treatment as described in the example below), a combination of folinic acid, 5-fluorouracil and irinotecan (i.e. the FOLFIRI treatment), or a combination of 5-fluorouracil and folinic acid (i.e. the FUFOL or LV5FU2 treatment).

In this regard the application WO2012146610 relates to a method of treatment of the mCRC by aflibercept, or ziv-aflibercept in combination with FOLFIRI. The content of this application is incorporated by reference.

In an embodiment of one of the methods described above therapeutically effective amounts of aflibercept, or ziv-aflibercept, oxaliplatin, 5-fluorouracil (5-FU) and folinic acid are administered to said patient.

In an embodiment of one of the methods described above therapeutically effective amounts of aflibercept, or ziv-aflibercept, folinic acid, 5-fluorouracil (5-FU) and irinotecan are administered to said patient.

In a further embodiment of one of the methods described above folinic acid at a dosage comprised between about 200 mg/m$^2$ and about 600 mg/m$^2$, 5-fluorouracil (5-FU) at a dosage comprised between about 2000 mg/m$^2$ and about 4000 mg/m$^2$, irinotecan at a dosage comprised between about 100 mg/m$^2$ and about 300 mg/m$^2$ and aflibercept at a dosage comprised between about 1 mg/kg and about 10 mg/kg are administered to patient.

In a further embodiment of one of the methods described above folinic acid at a dosage of about 400 mg/m$^2$, 5-fluorouracil (5-FU) at a dosage of about 2800 mg/m$^2$, irinotecan at a dosage of about 180 mg/m$^2$ and aflibercept at a dosage of about 4 mg/kg are administered to patient.

In a further embodiment of one of the methods described above folinic acid is administered intravenously at a dosage of about 400 mg/m$^2$, 5-fluorouracil (5-FU) is administered intravenously at a dosage of about 2800 mg/m$^2$, irinotecan is administered intravenously at a dosage of about 180 mg/m$^2$ and aflibercept is administered intravenously at a dosage of about 4 mg/kg and wherein the combination is administered every two weeks.

In a further embodiment of one of the methods described above folinic acid, 5-fluorouracil (5-FU), irinotecan and aflibercept are administered intravenously every two weeks for a period comprised between 9 and 18 weeks.

In a further embodiment of one of the methods described above folinic acid is administered intravenously immediately after aflibercept administration. It can be also administered intravenously immediately after aflibercept administration over a period of about 2 hours.

In a further embodiment of one of the methods described above irinotecan is administered intravenously immediately after aflibercept administration. It can be also administered intravenously immediately after aflibercept administration over a period of about 90 minutes.

In a further embodiment of one of the methods described above 5-fluorouracil (5-FU) is administered immediately after aflibercept administration.

In a further embodiment of one of the methods described above a first quantity of 5-fluorouracil (5-FU) is administered intravenously immediately after aflibercept administration and a second quantity of 5-FU is administered intravenously after the first quantity in continuous infusion.

In a further embodiment of one of the methods described above about 400 mg/m$^2$ of 5-fluorouracil (5-FU) is administered intravenously over a period of 2 to 4 minutes after aflibercept administration and wherein 2400 mg/m$^2$ of 5-FU is administered intravenously over around 46 hours after the administration of the 400 mg/m$^2$ in continuous infusion.

In an embodiment said patient has previously been treated with therapy based on oxaliplatin or on bevacizumab.

In another embodiment said patient has failed with chemotherapy, radiotherapy or surgery.

The invention relates also to aflibercept, or ziv-aflibercept for treating a patient suspected to suffer from cancer, wherein the IL-8 level in the patient's biological sample is lower than between around 15 and around 50 pg/ml.

The invention further relates to a kit for predicting whether a patient suspected to suffer from cancer is a candidate for aflibercept, or ziv-aflibercept therapy, which kit comprises:
  a) means for measuring the interleukin-8 (IL-8) level; and
  b) Optionally, a label giving instructions for the use of said kit in predicting whether a patient suspected to suffer from cancer is a candidate for aflibercept, or ziv-aflibercept therapy.

Another aspect of the invention further relates to an article of manufacture comprising:
  a) a packaging material;
  b) means for measuring the interleukin-8 (IL-8) level; and
  c) a label giving instructions for the use of said kit in predicting whether a patient suspected to suffer from cancer is a candidate for aflibercept, or ziv-aflibercept therapy.

The above methods and use of the invention may be, for instance, in vitro or ex vivo methods and use.

Means for measuring the expression level of IL8 protein are well-known in the art and include immunoassay such as ELISA assay. The means for measuring IL8 protein include antibodies specifically binding to IL8. Such means can be labeled with detectable compound such as fluorophores or radioactive compounds. For example, the probe or the antibody specifically binding to IL8 may be labeled with a detectable compound. Alternatively, when the kit comprises an antibody, the kit may further comprise a secondary antibody, labeled with a detectable compound, which binds to an unlabeled antibody specifically binding to IL8.

The means for measuring the expression level of IL8 may also include reagents such as e.g. reaction and/or washing buffers. The means may be present, e.g., in vials or microtiter plates, or be attached to a solid support such as a microarray as can be the case for primers and probes.

Aflibercept, or ziv-aflibercept is provided in a formulation which is not prejudicial to the patient to be treated.

In an embodiment aflibercept, or ziv-aflibercept is provided in a formulation with sucrose and polysorbate 20 (stabilisers), sodium chloride, citrate buffer, and sodium phosphate buffer, adjusted to final pH.

In another embodiment aflibercept, or ziv-aflibercept, is supplied in two drug product presentations:
  a presentation at 100 mg aflibercept, or ziv-aflibercept/4.0 mL (nominal concentration).
  a second presentation at 200 mg aflibercept, or ziv-aflibercept/8.0 mL (nominal concentration).

Both presentations are manufactured from the same bulk sterile solution at 25 mg/mL of aflibercept, or ziv-aflibercept.

Prior to infusion to the patient, the concentrate solution is diluted with 0.9% sodium chloride solution or 5% dextrose.

The anti-cancer agents used in the above recited method or use are provided in a pharmaceutically acceptable carrier, excipient or diluent which is not prejudicial to the patient to be treated.

Pharmaceutically acceptable carriers and excipient that may be used in the compositions of this invention include, but are not limited to, ion exchangers, alumina, aluminium stearate, lecithin, self-emulsifying drug delivery systems (SEDDS) such as d-a-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

As appreciated by skilled artisans, compositions are suitably formulated to be compatible with the intended route of administration. Examples of suitable routes of administration include parenteral route, including for instance intramuscular, subcutaneous, intravenous, intraperitoneal or local intratumoral injections. The oral route can also be used, provided that the composition is in a form suitable for oral administration, able to protect the active principle from the gastric and intestinal enzymes.

The terms "Therapy", "therapeutic", "treatment" and "treating" are used herein to characterize a therapeutic method or process that is aimed at (1) slowing down or stopping the progression, aggravation, or deterioration of the symptoms of the disease state or condition to which such term applies; (2) alleviating or bringing about ameliorations of the symptoms of the disease state or condition to which such term applies; and/or (3) reversing or curing the disease state or condition to which such term applies.

As used herein, the terms "interleukin-8" and "IL-8" are used interchangeably and refer to all of the naturally-occurring isoforms, including alternative splice variants, allelic variants and include naturally occurring variants, SNPs (single nucleotide polymorphisms), and truncated or secreted forms of IL-8 protein.

In particular, the terms "interleukin 8" refers to the polypeptide comprising or consisting of the amino acid sequence corresponding to the UniProtKB/Swiss-Prot accession number P10145 (SEQ ID NO: 2) and/or
  a) a polypeptide corresponding to the mature isoform of the polypeptide of (a) (i.e. obtained after cleavage of the signal peptide); and/or
  b) an allelic variant of the polypeptide of (a) or (b); and/or
  c) a splice variant of a polypeptide of (a), (b) or (c); and/or d) a constitutively active mutant of a polypeptide of (a), (b), (c) or (d).
e) an isoform obtained by proteolytic processing of a polypeptide of (a), (b), (c), (d) or (e).

By "isoform of a polypeptide" is meant a polypeptide that has at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid sequence identity to a full-length polypeptide reference sequence and has the same biological activity. In the context of the present application, the percentage of identity is calculated using a global alignment (i.e. the two sequences are compared over their entire length). Methods for comparing the identity of two or more sequences are well known in the art. The «needle» program, which uses the Needleman-Wunsch global alignment algorithm (Needleman and Wunsch, 1970 J. Mol. Biol. 48:443-453) to find the optimum alignment (including gaps) of two sequences when considering their entire length, may for example be used. The needle program is for example available on the ebi.ac.uk World Wide Web site. The percentage of identity in accordance with the invention can be calculated using the EMBOSS::needle (global) program with a "Gap Open" parameter equal to 10.0, a "Gap Extend" parameter equal to 0.5, and a Blosum62 matrix.

"Isoform" also refers to all post-translationally modified forms of IL8 protein. Post-translationally modified isoforms may include acetylated, formylated, lipoylated, myristoylated, palmitoylated, alkylated, methylated, amidated, glycosylated, hyrdroxylated, nitrosylated, phosphorylated, sulphated, polysialylated and sialylated forms.

The "reference level of expression of IL-8" may be determined as a single value or a range of values which is determined based on the expression level of IL-8 measured, for instance, in a population of healthy subjects or in a population of subjects in need of an aflibercept therapy.

In an embodiment the reference level of expression of IL-8 is determined based on the expression level of IL-8 measured in a population of subjects in need of a aflibercept therapy.

Typically, the analysed population could be divided into percentiles based on the measured level of expression of IL-8. The reference level could be defined as the percentile that provides the best separation between patients suffering from a cancer on which the treatment with aflibercept is efficient and patients suffering from a cancer on which the treatment with aflibercept is not efficient enough to cure it.

In the study reported in Example 1 below, the reference level of expression of IL-8 was 19 pg/ml (77th percentile).

However, the reference level of expression of IL-8 may vary i) according to the size of the studied population, and ii) depending on the method used for measuring the IL-8 expression.

The level of interleukin 8 protein may be, for instance, determined using immunological detection methods such as an ELISA assay. The methods involve an antibody which binds to interleukin 8 protein, for example a monoclonal or polyclonal antibody, an antibody variant or fragments such as a single chain antibody, a diabody, a minibody, a single chain Fv fragment (sc(Fv)), a Sc(Fv)2 antibody, a Fab fragment or a F(ab')2 fragment, or a single domain antibody. Such antibodies are well known in the art and are commercially available. They may also notably be obtained by immunization of animals (for example rabbits, rats or mice) with interleukin 8 protein. Antibodies may be used to determine protein expression in a range of immunological assays including competitive and non-competitive assay systems using techniques such as western blotting, immunohistochemistry/immunofluorescence (i.e protein detection on fixed cells or tissues), radioimmunoassay such as RIA (radio-linked immunoassay), ELISA (enzyme linked immunosorbent assay), "sandwich" immunoassays, immunoprecipitation assays, immunodiffusion assays, agglutination assays, complement-fixation assays, immunoradiometric assays, fluorescent immunoassays, e.g. FIA (fluorescence-linked immunoassay), chemiluminescence immunoassays, ECLIA (electrochemiluminescence immunoassay) and protein A immunoassays. Such assays are routine and well known to the person skilled in the art (Ausubel et al (1994) *Current Protocols in Molecular Biology*, Vol. 1, John Wiley & Sons, Inc., New York).

Protein expression of interleukin 8 may also be determined by proteomic method such as mass spectrometry assays (LC-MS or LC-MS/MS). Qualitative and quantitative mass spectrometric techniques are known and used in the art. To this aim, target peptides specific for marker proteins are selected and quantified based on calibration curves established with synthetic peptides labeled with stable isotopes. Enzymatic digests, spiked with a defined amount of isotope labeled target peptides, are analyzed by liquid chromatography coupled with mass spectrometry. The ratio between labeled and non-labeled target peptides is measured to assess target peptide concentrations and therefore protein marker concentration.

The expression "circulating IL8" is intended to mean the IL8 proteins present in blood, serum and plasma.

A "subject" or a "patient" may be a human or a non-human mammal, such as monkeys, dogs, cats, guinea pigs, hamsters, rabbits, cows, horses, goats and sheep.

BRIEF DESCRIPTION OF THE SEVERAL VIEWS OF THE DRAWINGS

FIG. 1 shows that high IL8 levels correlate with increased probability for disease progression and that this effect is slightly more pronounced in aflibercept versus FOLFOX treated patients. On the other hand, FIG. 2 shows that the increase in IL8 relative to baseline also corresponds to disease progression. Since increases in IL8 are plotted on a logarithmic scale, values between −3 and 0 correspond to an increase in IL8<1 pg/mL, whereas values between 0 and 3 represent increases>1 pg/mL. Data thus show that even small increases in IL8 relative to baseline already correspond to an increased probability of disease progression in the aflibercept arm.

DETAILED DESCRIPTION OF THE INVENTION

Figure 1:
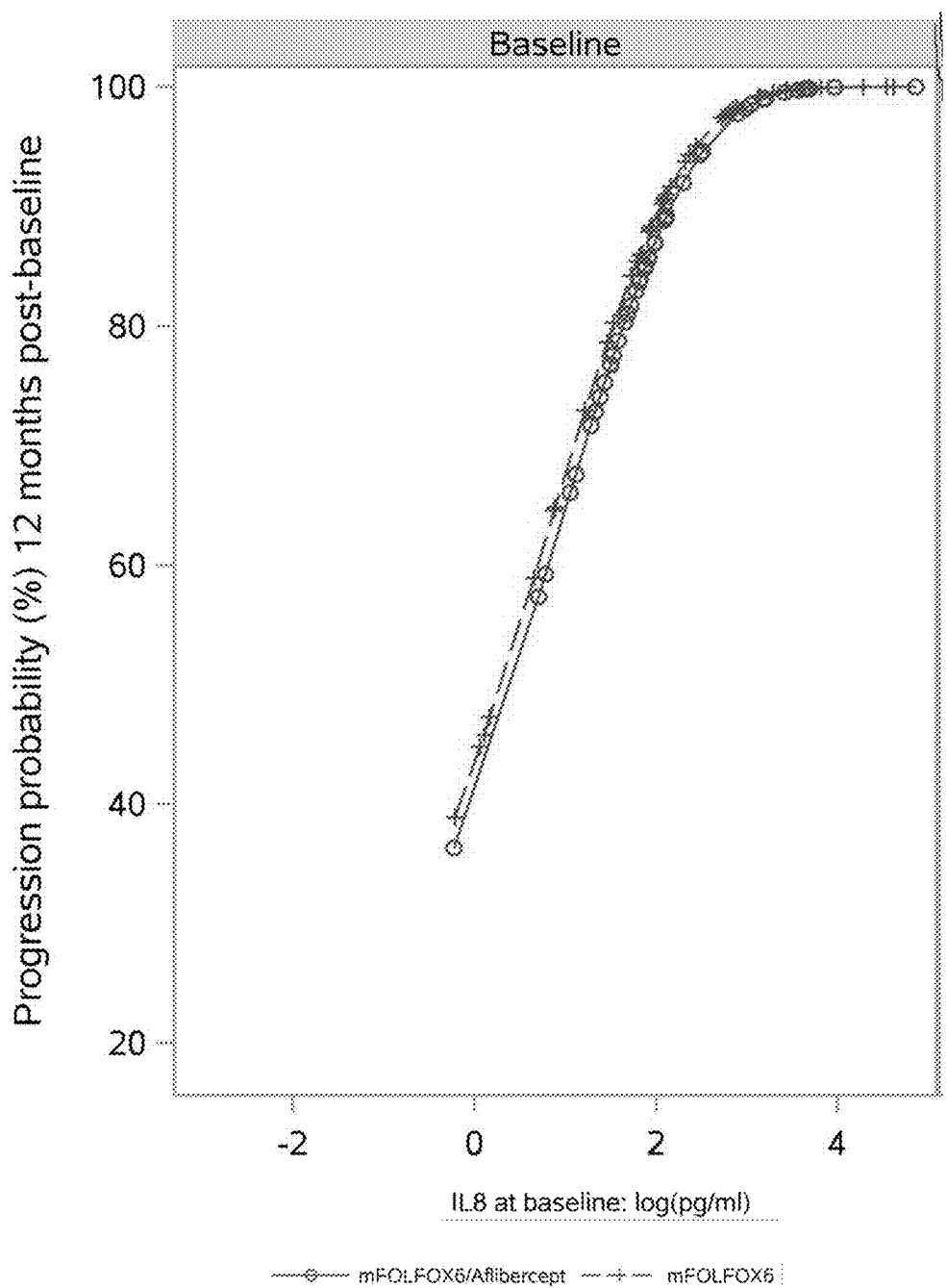
FIGS. 1 and 2 illustrate the relation between IL8 levels and the probability of disease progression. Depicted is the probability of disease progression after 12 months in relation to IL-8 plasma levels at baseline (FIG. 1) and the difference between IL8 plasma levels at baseline and the last measurement point before disease progression (FIG. 2). Briefly.

Example: Effect of Interleukin 8 on PFS in the AFFIRM Study

Study ECF10668 (AFFIRM)

EFC10668 was designed as a randomized, multinational, study comparing the adverse effects occurrence in patient with metastatic colorectal cancer (MCRC) treated with:

i) a modified FOLFOX6 (a combination of oxaliplatin, 5-fluorouracil (5-FU) and folinic acid) given intravenously every 2 weeks as first-line treatment (arm A); or ii) aflibercept at 4 mg/kg combined with a modified FOLFOX6 given intravenously every 2 weeks as first-line treatment; or Schedule of Administration Patients were administered intravenously either with aflibercept immediately followed by oxaliplatin, 5-fluorouracil (5-FU) and folinic acid (modified FOLFOX6 regimen) or modified FOLFOX6 alone, depending on arm to which they were assigned, This treatment was repeated every 2 weeks until progression (or unacceptable toxicity, or consent withdrawal).

Dosage

The patients randomized in the aflibercept arm received 4 mg/kg IV every 2 weeks.

The following were administered to patients in both treatment groups:
Oxaliplatin (Eloxatin®)
Folinic acid (also known as leucovorin)
5-fluorouracil
Formulations of oxaliplatin, 5-fluorouracil, and folinic acid:
  Products used were those available in the hospital/clinic pharmacy
  Route of administration: IV
  Dose: Oxaliplatin, folinic acid, and 5-fluorouracil were administered according to an mFOLFOX6 regimen, as follows:
    Oxaliplatin 85 mg/m$^2$ as a 2-hour IV infusion on day 1
    Folinic acid 350 mg/m$^2$ as a 2-hour IV infusion on day 1
    5-fluorouracil 400 mg/m$^2$ as an IV bolus on day 1, and then 2400 mg/m$^2$ as a 46-hour continuous IV infusion starting on day 1

In case of body surface area>2.0 m$^2$, the actual doses of oxaliplatin and of 5-FU were to be adjusted to a maximum BSA of 2.0 m$^2$ for safety reasons. Dose reduction and/or treatment delay and/or treatment discontinuation were planned in case of severe toxicity. The modified FOLFOX6 regimen was administered after administration of aflibercept.

Duration of Treatment

Treatment for an individual patient was administered up until progression or until unacceptable toxicity occurred or the patient withdrew consent.

Treatment duration was estimated to be approximately 12 months.

Demographics and Baseline Characteristics

Table 1 below compares demographics and patient characteristics at baseline between biomarkers evaluable and non-evaluable populations.

The "biomarkers evaluable population" is defined as the population of patients who provided a blood/tumor sample for biomarker assessment; while the "biomarkers non evaluable population" corresponds to patients who did not provide blood/tumor sample for biomarker assessment (e.g. patients who did not consent to biomarker study).

All characteristics are similar between populations, except for the region of origin of the patients: Eastern Europe tends to be over-represented and other countries tend to be under-represented in the biomarkers evaluable population compared to the biomarker non evaluable population.

TABLE 1

Summary of patient demographics and patient characteristics at baseline-Evaluable population

| | Biomarkers non evaluable population | | Biomarkers evaluable population | | |
|---|---|---|---|---|---|
| | mFolfox6 (N = 57) | Aflibercept/ mFolfox6 (N = 49) | mFolfox6 (N = 60) | Aflibercept/ mFolfox6 (N = 70) | p-value |
| Gender [n(%)] | | | | | 1.0000[a] |
| Number | 57 | 49 | 60 | 70 | |
| Male | 32 (56.1%) | 33 (67.3%) | 36 (60.0%) | 43 (61.4%) | |
| Female | 25 (43.9%) | 16 (32.7%) | 24 (40.0%) | 27 (38.6%) | |
| Age (Years) | | | | | 0.2811[b] |
| Number | 57 | 49 | 60 | 70 | |
| Median | 66.0 | 62.0 | 62.0 | 62.5 | |
| Mean | 63.7 | 61.8 | 61.3 | 61.7 | |
| (SD) | (10.0) | (9.5) | (9.4) | (8.7) | |
| Min:Max | 44:87 | 29:75 | 37:81 | 41:79 | |
| Age class [n(%)] | | | | | 0.2421[a] |
| Number | 57 | 49 | 60 | 70 | |
| <65 | 27 (47.4%) | 28 (57.1%) | 38 (63.3%) | 42 (60.0%) | |
| ≥65 but <75 | 23 (40.4%) | 20 (40.8%) | 20 (33.3%) | 25 (35.7%) | |
| ≥75 | 7 (12.3%) | 1 (2.0%) | 2 (3.3%) | 3 (4.3%) | |
| Race [n(%)] | | | | | 0.0640[a] |
| Number | 57 | 49 | 60 | 70 | |
| Caucasian/ White | 41 (71.9%) | 37 (75.5%) | 49 (81.7%) | 60 (85.7%) | |
| Black | 0 | 0 | 0 | 1 (1.4%) | |
| Asian/ Oriental | 16 (28.1%) | 11 (22.4%) | 11 (18.3%) | 9 (12.9%) | |
| Other | 0 | 1 (2.0%) | 0 | 0 | |
| Region | | | | | 0.0029[a] |
| Number | 57 | 49 | 60 | 70 | |
| Western Europe | 37 (64.9%) | 30 (61.2%) | 37 (61.7%) | 45 (64.3%) | |
| Eastern Europe | 3 (5.3%) | 3 (6.1%) | 12 (20.0%) | 12 (17.1%) | |
| Other countries | 17 (29.8%) | 16 (32.7%) | 11 (18.3%) | 13 (18.6%) | |
| BSA (m2) | | | | | 0.1091[b] |
| Number | 57 | 49 | 60 | 70 | |
| Median | 1.8 | 1.8 | 1.8 | 1.8 | |
| Mean (SD) | 1.7 (0.2) | 1.8 (0.2) | 1.8 (0.2) | 1.8 (0.2) | |
| Min:Max | 1:2 | 1:2 | 1:2 | 1:2 | |
| Weight (kg) | | | | | 0.0838[b] |
| Number | 57 | 49 | 60 | 70 | |
| Median | 67.6 | 70.0 | 73.2 | 71.4 | |
| Mean (SD) | 67.3 (14.1) | 71.1 (16.6) | 74.0 (17.0) | 71.5 (15.6) | |
| Min:Max | 40:107 | 40:115 | 48:134 | 40:117 | |

[a]comparing frequency distribution based on Fisher's exact test-2-sided.
[b]Using ANOVA (type 3) with factors: BIOPOP, BIOPOP. Records with missing values for factors or response were excluded from statistical analyses.
Frequency distribution of covariates is compared between evaluable and non-evaluable populations
Note:
Western Europe = Germany, Italy, Spain, United Kingdom; Eastern Europe = Russian Federation; Other countries = Australia, Korea

Disease Characteristics at Baseline

Disease characteristics at baseline were similar in the two populations (see Tables 2 and 3 below).

TABLE 2

Summary of disease characteristics at initial diagnosis

|  | Biomarkers non evaluable population | | Biomarkers evaluable population | | |
| --- | --- | --- | --- | --- | --- |
|  | mFolfox6 (N = 57) | Aflibercept/ mFolfox6 (N = 49) | mFolfox6 (N = 60) | Aflibercept/ mFolfox6 (N = 70) | p-value |
| Primary site [n(%)] |  |  |  |  | 0.7045[a] |
| Number | 57 | 49 | 60 | 70 |  |
| Colon | 27 (47.4%) | 26 (53.1%) | 31 (51.7%) | 33 (47.1%) |  |
| Recto sigmoid | 9 (15.8%) | 15 (30.6%) | 16 (26.7%) | 19 (27.1%) |  |
| Rectum | 21 (36.8%) | 8 (16.3%) | 13 (21.7%) | 18 (25.7%) |  |
| Histology type [n(%)] |  |  |  |  |  |
| Number | 57 | 49 | 60 | 70 |  |
| Adeno-carcinoma | 57 (100%) | 49 (100%) | 60 (100%) | 70 (100%) |  |
| Staging at diagnosis [n(%)] |  |  |  |  | 0.2297[a] |
| Number | 56 | 48 | 57 | 68 |  |
| Stage I | 1 (1.8%) | 0 | 2 (3.5%) | 2 (2.9%) |  |
| Stage II | 2 (3.6%) | 1 (2.1%) | 6 (10.5%) | 4 (5.9%) |  |
| Stage III | 5 (8.9%) | 3 (6.3%) | 3 (5.3%) | 4 (5.9%) |  |
| Stage IV | 48 (85.7%) | 44 (91.7%) | 46 (80.7%) | 58 (85.3%) |  |
| Time from diagnosis to randomization (months)* |  |  |  |  | 0.6620[b] |
| Number | 57 | 49 | 60 | 69 |  |
| Median | 1.4 | 1.8 | 1.6 | 1.7 |  |
| Mean (SD) | 12.6 (30.9) | 9.2 (16.9) | 9.8 (19.8) | 9.7 (17.5) |  |
| Min:Max | 0:149 | 0:80 | 0:84 | 0:80 |  |

[a]comparing frequency distribution based on Fisher's exact test-2-sided.
[b]Using ANOVA (type 3) with factors: BIOPOP, BIOPOP. Records with missing values for factors or response were excluded from statistical analyses.
Frequency distribution of covariates is compared between evaluable and non-evaluable populations
*If the day of initial date of diagnosis is missing, it is considered as the first day of the month

TABLE 3

Summary of organs involved at baseline

|  | Biomarkers non evaluable population | | Biomarkers evaluable population | | |
| --- | --- | --- | --- | --- | --- |
|  | mFolfox6 (N = 57) | Aflibercept/ mFolfox6 (N = 49) | mFolfox6 (N = 60) | Aflibercept/ mFolfox6 (N = 70) | p-value |
| Number of metastatic organs involved at baseline (excluding primary site) [n(%)] |  |  |  |  | 0.1711[a] |
| Number | 57 | 49 | 60 | 70 |  |
| 0 | 0 | 0 | 1 (1.7%) | 0 |  |
| 1 | 16 (28.1%) | 15 (30.6%) | 15 (25.0%) | 12 (17.1%) |  |
| >1 | 41 (71.9%) | 34 (69.4%) | 44 (73.3%) | 58 (82.9%) |  |
| Metastatic organs involved at baseline (excluding primary site) [n(%)]* | 57 (100%) | 49 (100%) | 59 (98.3%) | 70 (100%) |  |
| Liver | 44 (77.2%) | 42 (85.7%) | 47 (78.3%) | 57 (81.4%) |  |
| Lung | 27 (47.4%) | 18 (36.7%) | 25 (41.7%) | 28 (40.0%) |  |
| Lymph nodes | 26 (45.6%) | 25 (51.0%) | 30 (50.0%) | 38 (54.3%) |  |
| Muscle/ soft tissue | 9 (15.8%) | 6 (12.2%) | 14 (23.3%) | 10 (14.3%) |  |
| Peritoneum | 8 (14.0%) | 7 (14.3%) | 8 (13.3%) | 16 (22.9%) |  |
| Pleura | 5 (8.8%) | 7 (14.3%) | 2 (3.3%) | 1 (1.4%) |  |
| Adrenal | 2 (3.5%) | 0 | 1 (1.7%) | 1 (1.4%) |  |
| Bone | 2 (3.5%) | 1 (2.0%) | 4 (6.7%) | 4 (5.7%) |  |
| Kidneys | 1 (1.8%) | 0 | 0 | 0 |  |
| Spleen | 1 (1.8%) | 1 (2.0%) | 1 (1.7%) | 1 (1.4%) |  |
| Bladder | 0 | 0 | 1 (1.7%) | 1 (1.4%) |  |
| Metastatic organs involved at baseline class (excluding primary site) [n(%)] |  |  |  |  | 0.3536[a] |
| Number | 57 | 49 | 60 | 70 |  |
| No liver metastasis, or liver and other metastases | 49 (86.0%) | 39 (79.6%) | 51 (85.0%) | 63 (90.0%) |  |
| Liver metastasis only | 8 (14.0%) | 10 (20.4%) | 9 (15.0%) | 7 (10.0%) |  |

[a]comparing frequency distribution based on Fisher's exact test-2-sided. Records with missing values for factors or response were excluded from statistical analyses.
Frequency distribution of covariates is compared between evaluable and non-evaluable populations
*Percentages are not additive (sum greater than 100%)

Safety Evaluation

A. Extent of Exposure

Table 4 below shows that patients in the biomarkers evaluable population were exposed slightly longer to treatment than patients in the biomarkers non-evaluable population (median number of cycles: 12 versus 9 or 10).

There was no difference in exposure between treatment arms in the biomarkers evaluable population.

TABLE 4

Summary of overall study treatment exposure

|  | Biomarkers non evaluable population | | Biomarkers evaluable population | |
| --- | --- | --- | --- | --- |
|  | mFolfox6 (N = 56) | Aflibercept/ mFolfox6 (N = 49) | mFolfox6 (N = 60) | Aflibercept/ mFolfox6 (N = 70) |
| Number of cycles received by patient | | | | |
| Sum | 614 | 572 | 770.0 | 865.0 |
| Mean (SD) | 11.0 (7.0) | 11.7 (9.5) | 12.8 (7.0) | 12.4 (7.9) |
| Median | 10.0 | 9.0 | 12.0 | 12.0 |
| Min:Max | 1:43 | 1:44 | 3:33 | 1:42 |
| Number of cycles received by patient | | | | |
| 1 | 2 (3.6%) | 3 (6.1%) | 0 | 2 (2.9%) |
| 2 | 2 (3.6%) | 2 (4.1%) | 0 | 2 (2.9%) |
| 3 | 3 (5.4%) | 1 (2.0%) | 2 (3.3%) | 2 (2.9%) |
| 4 | 3 (5.4%) | 4 (8.2%) | 5 (8.3%) | 8 (11.4%) |
| 5 | 1 (1.8%) | 0 | 1 (1.7%) | 2 (2.9%) |
| 6 | 1 (1.8%) | 6 (12.2%) | 0 | 4 (5.7%) |
| 7 | 1 (1.8%) | 5 (10.2%) | 1 (1.7%) | 3 (4.3%) |
| 8 | 6 (10.7%) | 1 (2.0%) | 11 (18.3%) | 2 (2.9%) |
| 9 | 6 (10.7%) | 3 (6.1%) | 0 | 5 (7.1%) |
| 10 | 5 (8.9%) | 2 (4.1%) | 4 (6.7%) | 3 (4.3%) |
| 11-15 | 16 (28.6%) | 11 (22.4%) | 21 (35.0%) | 13 (18.6%) |
| 16-20 | 7 (12.5%) | 4 (8.2%) | 6 (10.0%) | 14 (20.0%) |
| 21-25 | 1 (1.8%) | 3 (6.1%) | 5 (8.3%) | 6 (8.6%) |
| >25 | 2 (3.6%) | 4 (8.2%) | 4 (6.7%) | 4 (5.7%) |
| Duration of exposure (weeks) | | | | |
| Number | 56 | 49 | 60 | 70 |
| Mean (SD) | 25.2 (16.0) | 27.5 (22.4) | 29.5 (16.4) | 28.7 (18.7) |
| Median | 24.1 | 23.1 | 27.3 | 25.4 |
| Min:Max | 2:95 | 2:106 | 6:77 | 2:88 |

Duration of exposure = ((First date of last cycle + 14)-First date of first cycle)/7
SD: standard deviation

B. Plasma Profiling

The plasma concentration of 27 cytokines, growth factors or soluble receptors was determined by enzyme-linked immunosorbent assays (ELISA) using two Fluorokine® MAP kits (the human angiogenesis panel A and the human high sensitivity cytokine panel; R&D Systems). Competition experiments were conducted to test interference of aflibercept with the detection of VEGF-A, VEGF-D and placental growth factor (PlGF). Angiopoietin-2 (ANGPT2), SDF1-α, HGF, VEGF-C, soluble VEGF receptor 3 (sFLT4, sVEGFR3) and sVEGFR2 were assessed by single ELISA (R&D Systems). Plasma markers were analyzed at baseline, at 30 and 60 days after the first study treatment infusion and 30 days after the last aflibercept infusion.

Statistical Analysis

Differences between patients with evaluable biomarkers and patients without evaluable biomarkers were assessed using a two-sided Fisher's exact test for categorical variables and ANOVA for continuous variables. Biomarkers were analyzed as quantitative variables, by coding the absence or presence of a somatic mutation as 0 or 1, and SNP genotypes as 0, 1 or 2 depending on the number of minor alleles present. The linear effects of baseline biomarkers on PFS were assessed using a Cox proportional hazard model with the following co-variates: Eastern Cooperative Oncology Group (ECOG) performance status (0-1 versus 2), liver-only metastases (yes/no), and the number of distant metastasis organs (1 versus >1), a treatment effect, a biomarker effect and a biomarker-treatment interaction effect. The significance of the latter two effects was jointly tested by a two-degrees-of-freedom Wald test. Extended statistical methods are described in supplementary methods.

Results

Of the 236 patients in the ITT population of the AFFIRM trial 227 (96%) were evaluable for response. Of these, 130 (57%) provided at least one biological sample, 60 (46%) and 70 (54%) of which participated in the mFOLFOX6 and mFOLFOX6 plus aflibercept arms, respectively. There was no major difference at a false discovery rate (FDR)-adjusted P-value of 0.05 between patients who provided a biological sample and those who did not in terms of patient biometrics, ethnicity, and disease characteristics at baseline, or at efficacy and safety endpoints (Table 1). Of those who provided at least one biological sample, 51 (39%) provided samples for each of the 3 biomarker types, with 88 (68%) and 97 (74%) patients providing samples for 2 or 1 of the biomarker types respectively. Each biomarker type was analyzed separately, to avoid patient groups that were too small for sub-analyses.

Profiling of Plasma Markers for Efficacy

Plasma levels of 27 markers were measured at different time points (i.e., at baseline [87 patients]; 30 and 60 days after start of treatment [82 and 73 patients]; and 30 days after the last treatment [56 patients] as indicated on Table 5.

TABLE 5

Number of observations per time point-total, below limit of quantification (LOQ) and of detection (LOD)

|  | Baseline | | | Day 30 | | | Day 60 | | | EOT + 30 Days | | |
| --- | --- | --- | --- | --- | --- | --- | --- | --- | --- | --- | --- | --- |
|  | Total | <LOQ | <LOD | Total | <LOQ | <LOD | Total | <LOQ | <LOD | Total | <LOQ | <LOD |
| ANGPT1 | 87 | 1 | 1 | 80 | 1 | 0 | 73 | 0 | 0 | 56 | 0 | 0 |
| ANGPT2 | 86 | 1 | | 82 | 1 | | 72 | 0 | | 55 | 1 | |
| CSF2 | 84 | 28 | 17 | 80 | 38 | 16 | 72 | 32 | 17 | 54 | 25 | 16 |
| CXCL12 | 86 | 0 | 0 | 82 | 2 | 2 | 72 | 0 | 0 | 55 | 0 | 0 |
| FGF1 | 87 | 14 | 14 | 80 | 16 | 16 | 73 | 18 | 18 | 56 | 8 | 8 |
| Endostatin | 87 | | | 80 | | | 73 | | | 56 | | |
| FGF2 | 87 | 19 | 11 | 80 | 20 | 15 | 73 | 19 | 11 | 56 | 10 | 5 |
| FlGF | 87 | 12 | 12 | 80 | 4 | 4 | 73 | 1 | 1 | 56 | 1 | 1 |
| HGF | 86 | 0 | 0 | 82 | 7 | 7 | 72 | 1 | 1 | 55 | 1 | 1 |

TABLE 5-continued

Number of observations per time point-total, below limit of quantification (LOQ) and of detection (LOD)

| | Baseline | | | Day 30 | | | Day 60 | | | EOT + 30 Days | | |
|---|---|---|---|---|---|---|---|---|---|---|---|---|
| | Total | <LOQ | <LOD | Total | <LOQ | <LOD | Total | <LOQ | <LOD | Total | <LOQ | <LOD |
| IFNG | 84 | 6 | 4 | 80 | 8 | 3 | 72 | 6 | 2 | 54 | 11 | 8 |
| IL10 | 84 | 0 | 0 | 80 | 1 | 1 | 72 | 2 | 2 | 54 | 0 | 0 |
| IL12 | 84 | 3 | 3 | 80 | 1 | 1 | 72 | 3 | 3 | 54 | 8 | 7 |
| IL1B | 84 | 1 | 1 | 80 | 0 | 0 | 72 | 1 | 1 | 54 | 4 | 4 |
| IL2 | 84 | 3 | 2 | 80 | 3 | 1 | 72 | 1 | 1 | 54 | 8 | 6 |
| IL4 | 84 | 2 | 2 | 80 | 1 | 1 | 72 | 2 | 2 | 54 | 7 | 7 |
| IL5 | 84 | 2 | 1 | 80 | 3 | 0 | 72 | 1 | 0 | 54 | 1 | 1 |
| IL6 | 84 | 0 | 0 | 80 | 2 | 1 | 72 | 0 | 0 | 54 | 1 | 1 |
| IL8 | 84 | 0 | 0 | 80 | 1 | 1 | 72 | 0 | 0 | 54 | 0 | 0 |
| PGF | 87 | 8 | 8 | 80 | 6 | 6 | 73 | 2 | 2 | 56 | 1 | 1 |
| TNF | 84 | 2 | 1 | 80 | 2 | 1 | 72 | 1 | 0 | 54 | 2 | 1 |
| PDGFA | 87 | | | 80 | | | 73 | | | 56 | | |
| VEGFA | 84 | 6 | 1 | 80 | 4 | 1 | 72 | 2 | 0 | 54 | 4 | 0 |
| PDGFB | 87 | | | 80 | | | 73 | | | 56 | | |
| VEGFC | 86 | 1 | 1 | 82 | 0 | 0 | 72 | 0 | 0 | 55 | 1 | 0 |
| sFLT4 | 86 | 0 | 0 | 82 | 7 | 7 | 72 | 1 | 1 | 55 | 1 | 1 |
| THBS2 | 87 | | | 80 | | | 73 | | | 56 | | |
| sKDR | 86 | 0 | 0 | 82 | 7 | 7 | 72 | 1 | 1 | 55 | 1 | 1 |

All cytokines were measured in pg/ml, but some transformations were applied when necessary to obtain a symmetric distribution or smaller numerical values (ng/ml) for the association models, as depicted in table 6.

TABLE 6

Selected transformations of original plasma cytokine levels (pg/ml)

| Cytokine | Transformation |
|---|---|
| ANGPT1 | log |
| ANGPT2 | log |
| CSF2 | square root |
| CXCL12 | ng/ml |
| FGF1 | cubic root |
| Endostatin | log |
| FGF2 | square root |
| FIGF | cubic root |
| HGF | Log |
| IFNG | square root |
| IL10 | cubic root |
| IL12 | None |
| IL1B | cubic root |
| IL2 | square root |
| IL4 | None |
| IL5 | Log |
| IL6 | Log |
| IL8 | Log |
| PGF | ng/ml |
| TNF | square root |
| PDGFA | log |
| VEGFA | Log |
| PDGFB | log |
| VEGFC | Log |
| sFLT4 | square root(ng/ml) |
| THBS2 | log |
| sKDR | square root(ng/ml) |

We assessed the association of each plasma marker at baseline with PFS, while allowing for an interaction with treatment (Table 7). The lowest P-value was obtained for IL8 (P=0.0211; FDR=0.596 and P=0.0218 for interaction).

TABLE 7

Effect of baseline plasma biomarkers on PFS. The P-values associated to the joint effect, the FDR-corrected joint effect, the plasma biomarker and the biomarker with treatment interaction effect are shown.

| | P-values | | | |
|---|---|---|---|---|
| Protein | Joint effect | FDR-corrected joint effect | Plasma level effect | Treatment by plasma level effect |
| IL8 | 0.0221 | 0.5962 | 0.6701 | 0.0218 |
| THBS2 | 0.1408 | 0.6523 | 0.0545 | 0.2234 |
| CXCL12 | 0.1610 | 0.6523 | 0.0573 | 0.1640 |
| IL10 | 0.1669 | 0.6523 | 0.0647 | 0.1311 |
| Ang1 | 0.1768 | 0.6523 | 0.0724 | 0.0831 |
| FIGF | 0.1974 | 0.6523 | 0.6826 | 0.1704 |
| FGF2 | 0.2063 | 0.6523 | 0.1722 | 0.0768 |
| sVEGFR2 | 0.2171 | 0.6523 | 0.1616 | 0.0812 |
| PDGFA | 0.2474 | 0.6523 | 0.1155 | 0.1052 |
| IL6 | 0.2689 | 0.6523 | 0.1061 | 0.1838 |
| FGF1 | 0.3185 | 0.6523 | 0.4759 | 0.1536 |
| VEGF-A | 0.3202 | 0.6523 | 0.2549 | 0.7133 |
| CSF2 | 0.3272 | 0.6523 | 0.4278 | 0.1679 |
| IL12 | 0.3587 | 0.6523 | 0.3664 | 0.1808 |
| IFNg | 0.3855 | 0.6523 | 0.8662 | 0.2984 |
| IL4 | 0.3866 | 0.6523 | 0.7326 | 0.4796 |
| PlGF | 0.5008 | 0.7955 | 0.3018 | 0.2595 |
| PDGFB | 0.5442 | 0.8163 | 0.4795 | 0.2963 |
| IL1B | 0.6025 | 0.8439 | 0.3183 | 0.3595 |
| HGF | 0.6286 | 0.8439 | 0.3369 | 0.5093 |
| IL2 | 0.6564 | 0.8439 | 0.7696 | 0.4093 |
| Endostatin | 0.9021 | 0.9783 | 0.7429 | 0.9824 |
| sFLT4 | 0.9063 | 0.9783 | 0.6849 | 0.8668 |
| TNF | 0.9461 | 0.9783 | 0.8736 | 0.7442 |
| Ang2 | 0.9698 | 0.9783 | 0.9279 | 0.9747 |
| VEGF-C | 0.9772 | 0.9783 | 0.8375 | 0.8307 |
| IL5 | 0.9783 | 0.9783 | 0.8813 | 0.8501 |

The Cox model assumes a linear relationship between the plasma marker and the log of the PFS hazard function, but since this hypothesis may be violated when analyzing continuous markers that vary considerably, a threshold effect may be more relevant. We explored this possibility by searching for the optimal cut-off level that maximizes the interaction with the treatment and the plasma marker. For IL8, the optimal cut-off was at 19 pg/ml (77$^{th}$ percentile). A model, in which IL8 was analyzed as a binary variable with this threshold, fitted better than a model with continuous IL8 levels (AIC of 469.3 versus 477.6). Patients with low IL8 levels (≥19 pg/ml, 77% of patients) exhibited a longer PFS in the aflibercept/mFLOFOX6 arm than in the mFOLFOX6 arm (Table 8).

TABLE 8

Kaplan-Meier estimates of effect of biomarkers on months of PFS.

|  | mFOLFOX6 Median (99% CI) | Aflibercept plus mFOLFOX6 Median (99% CI) | Hazard Ratio vs mFOLFOX6 (99% CI) |
|---|---|---|---|
| Plasma protein markers |  |  |  |
| All patients | 8.8 (6.57-10.02) | 8.5 (6.67-10.05) | 0.979 (0.505-1.897) |
| IL8 ≤ 19 pg/mL | 8.8 (5.62-10.91) | 9.3 (7.52-11.10) | 0.764 (0.363-1.607) |
| IL8 > 19 pg/mL | 8.8 (5.09-15.64) | 4.1 (2.33-8.54) | 2.71 (0.735-9.984) |

CI, confidence interval; mt, mutant; wt, wild-type.

Figure 2:
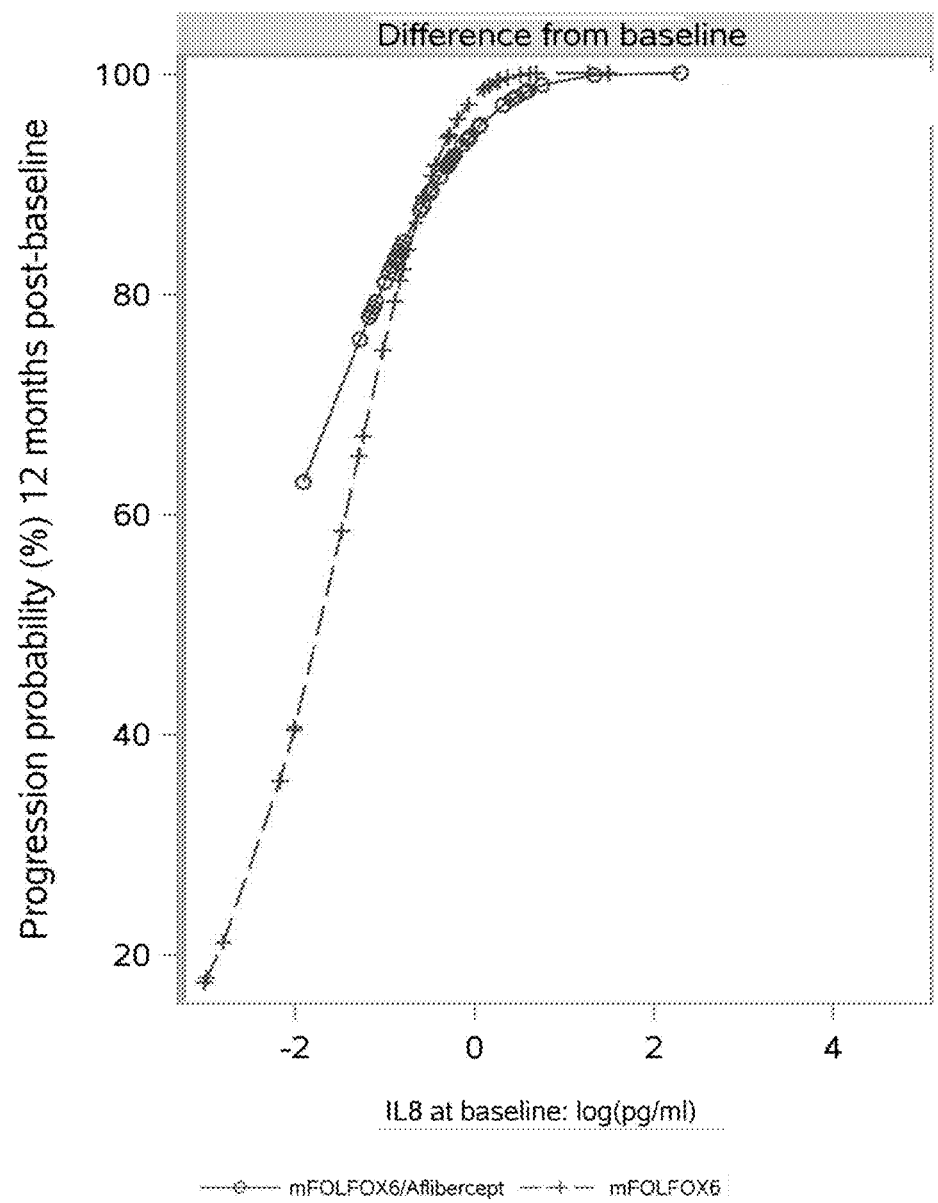

We also analyzed whether treatment-related changes in plasma markers could predict aflibercept treatment outcome. The Cox model included the effect of baseline plasma levels and the difference in expression measured at baseline and the last time point before discontinuation, disease progression or death (i.e., at 30 days or 60 days of treatment), while allowing for interaction with the treatment arm. IL8 was the only marker with a significant effect of change from baseline on PFS (P=0.0018; FDR=0.0478; Table 9). This effect did not differ between treatment arms (P=0.2028). High baseline or post-baseline increased IL8 levels corresponded to a higher probability of disease progression at 12 months (FIGS. 1 and 2).

TABLE 9

Effect of plasma marker changes from baseline on PFS. P-values (and FDR) of the joint effects of plasma marker and treatment by plasma marker interactions are shown. P-values for the change from baseline and the interaction are also presented.

| | P-values | | | |
|---|---|---|---|---|
| Protein | Joint effect | Joint effect FDR-corrected | Change from baseline effect | Treatment by Change from baseline effect |
| IL8 | 0.0018 | 0.0478 | 0.0006 | 0.2028 |
| IL10 | 0.0342 | 0.4525 | 0.5214 | 0.8204 |
| VEGFA | 0.0619 | 0.4525 | 0.0189 | 0.0704 |

TABLE 9-continued

Effect of plasma marker changes from baseline on PFS. P-values (and FDR) of the joint effects of plasma marker and treatment by plasma marker interactions are shown. P-values for the change from baseline and the interaction are also presented.

| | P-values | | | |
|---|---|---|---|---|
| Protein | Joint effect | Joint effect FDR-corrected | Change from baseline effect | Treatment by Change from baseline effect |
| CXCL12 | 0.0670 | 0.4525 | 0.1714 | 0.0318 |
| CSF2 | 0.0855 | 0.4619 | 0.0266 | 0.1682 |
| VEGFC | 0.1127 | 0.5072 | 0.0742 | 0.9355 |
| IL5 | 0.1886 | 0.7275 | 0.0684 | 0.1657 |
| Endostatin | 0.2418 | 0.7882 | 0.9988 | 0.2668 |
| PDGFA | 0.3092 | 0.7882 | 0.1508 | 0.9922 |
| TNF | 0.3209 | 0.7882 | 0.1770 | 0.1554 |
| IL4 | 0.3211 | 0.7882 | 0.1938 | 0.7631 |
| FGF2 | 0.3851 | 0.8191 | 0.6468 | 0.3957 |
| sFLT4 | 0.3944 | 0.8191 | 0.2533 | 0.1729 |
| THBS2 | 0.4677 | 0.8426 | 0.2387 | 0.6683 |
| FGF1 | 0.4770 | 0.8426 | 0.4669 | 0.2242 |
| PGF | 0.4993 | 0.8426 | 0.2501 | 0.2755 |
| ANGPT2 | 0.5638 | 0.8924 | 0.3373 | 0.8394 |
| IL1B | 0.6261 | 0.8924 | 0.3345 | 0.5414 |
| PDGFB | 0.6583 | 0.8924 | 0.3730 | 0.6009 |
| IL12 | 0.6611 | 0.8924 | 0.7934 | 0.7744 |
| IL2 | 0.7984 | 0.9482 | 0.9352 | 0.6027 |
| sKDR | 0.8375 | 0.9482 | 0.6009 | 0.5613 |
| HGF | 0.8383 | 0.9482 | 0.5804 | 0.5665 |
| IFNG | 0.8559 | 0.9482 | 0.6923 | 0.9101 |
| ANGPT1 | 0.8814 | 0.9482 | 0.6269 | 0.8538 |
| FIGF | 0.9131 | 0.9482 | 0.6838 | 0.7528 |
| IL6 | 0.9963 | 0.9963 | 0.9893 | 0.9594 |

When plasma biomarkers were measured at baseline only, IL8 had the most prominent effect on PFS, which was best described as a threshold effect with high circulating IL8 (IL8>19 pg/mL) associated with a shorter PFS in the aflibercept-treated patients.

When plasma biomarkers were measured at baseline and during treatment, high levels of circulating IL8 at baseline together with increased levels of IL8 measured during treatment were significantly associated with reduced PFS (FDR=0.0478).

Conclusions

We identified that high IL8 levels at baseline correlated with shorter survival times, and patients with increasing levels of IL8 during treatment were more likely to progress.

This suggests that patients with high IL8 levels, at baseline or during treatment, are at increased risk of disease progression during aflibercept therapy.

The invention claimed is:

1. A method of determining the therapeutic efficacy of aflibercept or ziv-aflibercept in a patient with colon cancer, colorectal cancer, or rectal cancer, comprising subjecting a biological sample from the patient to at least one assay to measure the IL-8 expression level in the biological sample, and comparing the measured IL-8 expression level to a reference level of IL-8, wherein an IL-8 expression level measured in the biological sample lower than the reference level is indicative of the therapeutic efficacy of aflibercept in said patient.

2. The method of claim 1, wherein the colon cancer is metastatic colon cancer.

3. The method of claim 1, wherein the colorectal cancer is metastatic colorectal cancer.

4. The method of claim 1, wherein the rectal cancer is metastatic rectal cancer.

5. The method of claim 1, wherein the reference level of IL-8 is between about 10 and about 30 pg/mL.

6. The method of claim 1, wherein the reference level of IL-8 is about 19 pg/mL.

7. The method of claim 1, wherein the biological sample is selected from the group consisting of blood, serum and plasma.

8. The method of claim 1, wherein the IL-8 level is a circulating level.

9. The method of claim 1, wherein the patient has previously been treated with oxaliplatin or bevacizumab.

10. The method of claim 1, wherein the reference level of IL-8 is the expression level of IL-8 in a subject without cancer.

* * * * *